US007371560B2

(12) United States Patent
Hankamer et al.

(10) Patent No.: US 7,371,560 B2
(45) Date of Patent: May 13, 2008

(54) PHOTOSYNTHETIC HYDROGEN PRODUCTION

(75) Inventors: Ben Hankamer, Kenmore (AU); Olaf Kruse, Bielefeld (DE)

(73) Assignee: University of Queensland, Brisbane (AU)

( * ) Notice: Subject to any disclaimer, the term of this patent is extended or adjusted under 35 U.S.C. 154(b) by 0 days.

(21) Appl. No.: 10/562,512

(22) PCT Filed: Jul. 7, 2004

(86) PCT No.: PCT/AU2004/000913

§ 371 (c)(1),
(2), (4) Date: Mar. 16, 2006

(87) PCT Pub. No.: WO2005/003024

PCT Pub. Date: Jan. 13, 2005

(65) Prior Publication Data

US 2006/0166343 A1   Jul. 27, 2006

(30) Foreign Application Priority Data

Jul. 7, 2003   (AU)   .............................. 2003903453

(51) Int. Cl.
*C12P 3/00* (2006.01)
*C12N 1/21* (2006.01)
*C07H 21/04* (2006.01)

(52) U.S. Cl. .............................. 435/257.6; 435/252.3; 435/253.6; 435/257.2; 435/168; 536/23.2

(58) Field of Classification Search ..................... None
See application file for complete search history.

(56) References Cited

OTHER PUBLICATIONS

Allen et al., "Chloroplasat Protein Phosphorylation Couples Plastoquinone Redox State to Distribution of Excitation Energy Between Photosystems," Nature, vol. 297, (May 7, 1981) pp. 25-29.
Bonaventure et al., "Fluorescence and Oxygen Evolution from *Chlorella pyrenoidosa*," Biochimica et Biophysica Acta, vol. 189, (1969) pp. 366-383.
Bulte et al., "ATP Control on State Transitions in vivo in *Chlamydomonas reinhardtii*," Biochimica et Biophysica Acta, vol. 1020, (1990) pp. 72-80.
Daga et al., "Molecular Characterization of the Transcription Termination Factor from Human Mitochondria," The Journal of Biological Chemistry, vol. 268, No. 11, (Apr. 15, 1993) pp. 8123-8130.
Day et al., "A Transposon with an Unusual Arrangement of Long Terminal Repeats in the Green Alga *Chlamydomonas reinhardtii*," The EMBO Journal., vol. 7, No. 7, (1988) pp. 1917-1927.
De Vitry et al., "Analysis of the Nucleus-Encoded and Chloroplast-Targeted Rieske Protein by Classic and Site-Directed Mutagenesis of Chlamydomonas," The Plant Cell, vol. 11, (Oct. 1999) pp. 2031-2044.

Debuchy et al., "The Argininosuccinate Lyase Gene of *Chlamydomonas reinhardtii*: An Important Tool for Nuclear Transformation and for Correlating the Genetic and Molecular Maps of the ARG7 Locus," The EMBO Journal, vol. 8, No. 10, (1989) pp. 2803-2809.
Depege et al., "Role of Chloroplast Protein Kinase Stt7 in LHCII Phosphorylation and State Transition in Chlamydomonas," Science, vol. 299, (Mar. 7, 2003) pp. 1572-1575.
Duby et al., "Alteration of Dark Respiration and Reduction of Phototrophic Growth in an Mitochondrial DNA Deletion Mutant of Chlamydomonas Lacking cob, nd4 and the 3' End of nd5," The Plant Cell, vol. 11, (Jan. 1999) pp. 115-125.
Dutilleul et al., "Functional Mitochondrial Complex I is Required by Tobacco Leaves for Optimal Photosynthetic Performance in Photorespiratory Conditions and During Transients," Plant Physiology, vol. 131, (Jan. 2003) pp. 264-275.
Fernandez-Silva et al., "The Human Mitochondrial Transcription Termination Factor (mTERF) is a Multizipper Protein but Binds to DNA as a Monomer, with Evidence Pointing to Intramolecular Leucine Zipper Interactions," The EMBO Journal, vol. 16, No. 5, (1997) pp. 1066-1079.
Finazzi et al., "Involvement of State Transitions in the Switch Between Linear and Cyclic Electron Flow in *Chlamydomonas reinhardtii*," EMBO Reports, vol. 3, No. 3, (2002) pp. 280-285.
Finazzi et al., "Thylakoid Targeting of Tat Passenger Proteins Shows no ΔpH Dependence in Vivo," The EMBO Journal, vol. 22, No. 4, (2003) pp. 807-815.
Fleischmann et al., "Isolation and Characterization of Photoautotrophic Mutants of *Chlamydomonas reinhardtii* Deficient in State Transition," The Journal of Biological Chemistry, vol. 274, No. 43, (Oct. 22, 1999) pp. 30987-30994.
Florin et al., "A Novel Type of Iron Hydrogenase in the Green Alga Scenedesmus Obliquus is Linked to the Photosynthetic Electron Transport Chain," The Journal of Biological Chemistry, vol. 276, No. 9, (Mar. 2, 2001) pp. 6125-6132.
Flugge, "Metabolite Transporters in Plastids," Plant Biology, vol. 1, (1998) pp. 201-206.
Gans et al., "The Effect of Cyanide on State Transition in Chlamydomonas reinhardtii," Biochimica et Biophysica Acta, vol. 1228, (1995) pp. 51-57.
Ghirardi et al., "Oxygen Sensitivity of Algal H2-Production," Applied Biochemistry and Biotechnology, vol. 63-65, (1997) pp. 141-151.

(Continued)

*Primary Examiner*—Ponnathapu Achutamurthy
*Assistant Examiner*—Md. Younus Meah
(74) *Attorney, Agent, or Firm*—Jennifer L. Skord; Moore & Van Allen PLLC

(57) ABSTRACT

A process for the production of hydrogen, comprising the steps of: (i) providing a photosynthetic microorganism having electron transfer capability through a photosynthetic light reaction pathway and through a respiratory electron transfer chain involving an oxidative phosphorylation pathway, and which expresses a hydrogenase, wherein regulation of the oxidative phosphorylation pathway is disrupted with the result that electron flow along the respiratory electron transfer chain toward cytochrome oxidase (complex IV) is reduced; ii) culturing the microorganism under microoxic and illuminated conditions; and (iii) collecting evolved hydrogen.

6 Claims, 16 Drawing Sheets

OTHER PUBLICATIONS

Ghirardi et al., "Microalgae: A Green Source of Renewable H2," Tibtech, vol. 18, (Dec. 2000) pp. 506-511.
Gray et al., "Organization and Expression of Algal (*Chlamydomonas reinhardtii*) Mitochondrial DNA," Biological Sciences, vol. 319, No. 1193 (May 31, 1998) pp. 135-147.
Gu et al., "Analysis of Leaf Sectors in the NCS6 Mitochondrial Mutant of Maize," The Plant Cell, vol. 5, (Aug. 1993) pp. 963-971.
Gumpel et al., "Playing Tag with Chlamydomonas," Trends in Cell Biology, vol. 4, (Aug. 1994) pp. 299-301.
Happe et al., "Differential Regulation of the Fe-Hydrogenase During Anaerobic Adaptation in the Green Alga *Chlamydomonas reinhardtii*," Eur. J. Biochem., vol. 269, (2002) pp. 1022-1032.
Heldt et al., "Alkalization of the Chloroplast Stroma Caused by Light-Dependent Proton Flux into the Thylakoid Space," Biochimica et Biophysica Acta, vol. 314, (1973) pp. 224-241.
Hess et al., "Impairment of the Mitochondrial Transcription Termination by a Point Mutation Associated with the MELAS Subgroup of Mitochondrial Encephlomyopathies," Nature, vol. 351, (May 16, 1991) pp. 236-239.
Hoefnagel et al., "Interdependence Between Chloroplasts and Mitochondria in the Light and the Dark," Biochimica et Biophysica Acta, vol. 1366, (1998) pp. 235-255.
Hoffert et al., "Energy Implications of Future Stabilization of Atmospheric CO2 Content," Nature, vol. 395, (Oct. 29, 1998) pp. 881-884.
Horton et al., "Regulation of Phosphorylation of Chloroplast Membrane Polypeptides by the Redox State of Plastoquinone," FEBS Letters, vol. 125, No. 2, (Mar. 1981) pp. 193-196.
Husic et al., "Inhibition of Glycolate and D-Lactate Metabolism in a *Chlamydomonas reinhardtii* Mutant Deficient in Mitochondrial Respiration," Proc. Natl. Acad. Sci. USA, vol. 84, (Mar. 1987) pp. 1555-1559.
Kindle et al., "Stable Nuclear Transformation of Chlamydomonas Using the Chlamydomonas Gene for Nitrate Reductase," The Journal of Cell Biology, vol. 109, No. 6, Pt. 1, (Dec. 1989) pp. 2589-2601.
Kromer et al., "Mitochondrial Oxidative Phosphorylation Participating in Photosynthetic Metabolism of a Leaf Cell," FEB, vol. 226, No. 2, (Jan. 1988) pp. 352-356.
Kromer et al., "On the Role of Mitochondrial Oxidative Phosphorylation in Photosynthesis Metabolism as Studied by the Effect of Oligomycin on Photosynthesis in Protoplasts and Leaves of Barley (*Hordeum vulagare*)," Plant Physiol., vol. 95, (1991) pp. 1270-1276.
Kruse, "Light-Induced Short-Term Adaptation Mechanisms Under Redox Control in the PS II-LHCII Supercomplex: LHC II State Transitions and PS II Repair Cycle," Naturwissenschaften, vol. 88, (2001) pp. 284-292.
Kruse et al., "Termination of Transcription in Human Mitochondria: Identification and Purification of a DNA Binding Protein Factor that Promotes Termination," Cell, vol. 58, (Jul. 28, 1989) pp. 391-397.
Kruse et al., "Isolation of State Transition Mutants of *Chlamydomonas reinhardtii* by Fluorescence Video Imaging," Photosynthesis Research, vol. 61, (1999) pp. 43-51.
Lee et al., "A New Oxygen Sensitivity and Its Potential Application in Photosynthetic H2 Production," Applied Biochemistry and Biotechnology, vol. 105-108, (2003) pp. 303-313.
Lemaire et al., "Characterization of Thioredoxin y, A New Type of Thioredoxin Identified in the Genome of *Chlamydomonas reinhardtii*," FEBS Letters, vol. 543, (2003) pp. 87-92.
Lown et al., "Chlamydomanas Nuclear Mutants that Fail to Assemble Respiratory or Photosynthetic Electron Transfer Complexes," Biochemical Society Transactions, vol. 29, Pt. 4, (2001) pp. 452-455.
Melis et al., "Hydrogen Production. Green Algae as a Source of Energy," Plant Physiology, vol. 127, (Nov. 2001) pp. 740-748.
Melis et al., "Sustained Photobiological Hydrogen Gas Production upon Reversible Inactivation of Oxygen Evolution in the Green Alga *Chlamydomonas reinhardtii*," Plant Physiology, vol. 122, (Jan. 2000) pp. 127-135.

Michel et al., "Molecular Characterization of idiA and Adjacent Genes in the *Cyanobacteria synechococcus* sp. Strains PCC 6301 and PCC 7942," Microbiology, vol. 145, (1999) pp. 1473-1484.
Millenaar et al., "The Role of the Alternative Oxidase in Stabilizing the in vivo Reduction State of the Ubiquinone Pool and the Activation State of the Alternative Oxidase," Plant Physiol., vol. 118, (1998) pp. 599-607.
Murata, "Control of Excitation Transfer in Photosynthesis," Biochimica et Biophysica Acta, vol. 172, (1969) pp. 242-251.
"National Hydrogen Energy Roadmap," United States Department of Energy, Natioal Hydrogen Energy Roadmap Workshop, Washington, DC, (Apr. 2-3, 2002) pp. 1-58.
Nelson et al., "The CRY1 Gene in *Chlamydomonas reinhardtii*: Structure and Use as a Dominant Selectable Marker for Nuclear Transformation," Molecular and Cellular Biology, vol. 14, No. 6, (Jun. 1994) pp. 4011-4019.
Nijtmans et al., "Assembly of Cytochrome-c Oxidase in Cultured Human Cells," Eur. J. Biochem, vol. 254, (1998) pp. 389-394.
Nurani et al., "Homologous and Heterologous Protein Import into Mitochondria Isolated from the Green Alga *Chlamydomonas reinhardtii*," Plant Molecular Biology, vol. 35, (1997) pp. 973-980.
Petit et al., "Climate and Atmospheric History of the Past 420,000 Years from the Vostok Ice Core, Antarctica," Nature, vol. 399, (Jun. 3, 1999) pp. 429-436.
Pfannschmidt et al., "Photosynthetic Control of Chloroplast Gene Expression," Nature, vol. 397, (Feb. 18, 1999) pp. 625-628.
Polosa et al., "Cloning and Characterisation of mtDBP, a DNA-Binding Protein Which Binds Two Distinct Regions of Sea Urchin Mitochondrial DNA," Nucleic Acids Research, vol. 27, No. 8, (1999) pp. 1890-1899.
Purton et al., "Charaterisation of the ARG7 Gene of *Chlamydomonas reinhardtii* and its Application to Nuclear Transformation," Eur. J. of Phycol., vol. 30, (1995) pp. 141-148.
Rasmusson et al., "Physiological, Biochemical and Molecular Aspects of Mitochondrial Complex I in Plants," Biochimica et Biophysica Acta, vol. 1364, (1998) pp. 101-111.
Rebeille et al., "Interaction Between Chloroplasts and Mitochondria in Microalgae," Plant Physiol., vol. 88, (1988) pp. 973-975.
Rintamaki et al., "Cooperative Regulation of Light-Harvesting Complex ll Phosphorylation via the Plastoquinol and Ferredoxin-Thioredoxin System in Chloroplasts," PNAS, vol. 97, No. 21, (Oct. 10, 2000) pp. 11644-11649.
Roberti et al., "DmTTF, A Novel Mitochondrial Transcription Termination Factor that Recognises Two Sequences of Drosophila Melanogaster Mitochodrial DNA," Nucleic Acids Research, vol. 31, No. 6, (2003) pp. 1597-1604.
Schonfeld et al., "The Nucleus-Encoded Protein MOC1 is Essential for Mitochondrial Light Acclimation in *Chlamydomonas reinhardtii*," The Journal of Biological Chemistry, vol. 279, No. 48, (Nov. 26, 2004) pp. 50366-50374.
Selwood et al., "Does the Mitochondrial Transcription-Termination Complex Play an Essential Role in Controlling Differential Transcription of Mitochondrial DNA?" Biochemical Society Transactions, vol. 28, Pt. 2, (2000) pp. 154-159.
Stephenson et al., "Hydrogenase: A Bacterial Enzyme Activating Molecular Hydrogen," Biochem, vol. XXV, (1931) pp. 205-214.
Strauss et al., "Ligation-Mediated Suppression-PCR as a Powerful Tool to Analyse Nuclear Gene Sequences in the Green Alga *Chlamydomonas reinhardtii*," Photosynthesis Research, vol. 70, (2001) pp. 311-320.
Svensson et al, "Light-Dependent Gene Expression for Proteins in the Respiratory Chain of Potato Leaves," The Plant Journal, vol. 28, No. 1, (2001) pp. 73-82.
Tam et al., "Cloning of Flagellar Genes in*Chlamydomonas reinhardtii* by DNA Insertional Mutagenesis," Genetics, vol. 135, (Oct. 1993) pp. 375-384.
Thomas et al., "Extinction Risk from Climate Change," Nature, vol. 427, (Jan. 8, 2004) pp. 145-148.
Trebst, "Inhibitors in Electron Flow: Tools for the Functional and Structural Localization of Carriers and Energy Conservation Sites," Methods in Enzymology, vol. 69, (1980) pp. 675-715.

Vener et al., "Plastoquinol at the Quinol Oxidation Site of Reduced Cytochrome bf Mediates Signal Transduction Between Light and Protein Phosphorylation: Thylakoid Protein Kinase Deactivation by a Single-Turnover Flash," PNAS, vol. 94, (1997) pp. 1585-1590.

Vener et al., "A Cyclophilin-Regulated PP2A-Like Protein Phosphatase in Thylakoid Membranes of Plant Chloroplasts," Biochemistry, vol. 38, (1999) pp. 14955-14965.

Verma et al., "Differential Regulation of High Light Tolerance in the Mutant and Wild-Type Anacystis Cells," Current Microbiology, vol. 30, (1995) pp. 373-379.

Wollman, "State Transitions Reveal the Dynamics and Flexibility of the Photosynthetic Apparatus," The EMBO Journal, vol. 20, No. 14, (2001) pp. 3623-3630.

Zerges et al., "Low Density Membranes are Associated with RNA-Binding Proteins and Thylakoids in the Chloroplast of *Chlamydomonas reinhardtii*," The Journal of Cell Biology, vol. 140, No. 1, (Jan. 12, 1998) pp. 101-110.

Zito et al., "The QO Site of Cytochrome b6f Complexes Controls the Activation of the LHCII Kinase," The EMBO Journal, vol. 18, No. 11, (1999) pp. 2961-2969.

European Supplementary Search Report for EP04737534.0 dated Jun. 12, 2007.

Kruse et al., "Improved Photobiological H2 Production in Engineered Green Algal Cells," The Journal of Biological Chemistry, vol. 280, No. 40, (Oct. 7, 2005), pp. 34170-34177.

Seibert et al., "Development of Selection and Screening Procedures for Rapid Identification of H2-Producing Algal Mutants with Increased O2 Tolerance," BioHydrogen, Plenum Press, New York, (1998), pp. 227-234.

Hippler, M. et al., Chlamydomonas genetics, a tool for the study of bioenergetic pathways. *Biochimica et Biophysica Acta* (1998) vol. 1367, pp. 1-62. See p. 43, right column and p. 53 right column to p. 54 left column.

Ghirardi, M.L. et al. Microalgae: a green source of renewable $H_2$. *Trends in Biotechnology* (2000) vol. 18, pp. 506-511.

Melis, A. et al. Sustained photobiological hydrogen gas prodution upon reversible inactivation of oxygen evolution in the green algae *Chlamydomonas reinhardtii*. *Plant Physiology* (2000) vol. 122 pp. 127-135.

Polle, J.E. W. et al. Truncated chlorophyll antenna size of the photosystems—a practical method to improve microalgal productivity and hydrogen production in mass culture. *International Journal of Hydrogen Energy* (2002) vol. 27, pp. 1257-1264.

a.

b.

c.

PHOTOSYNTHETIC HYDROGEN PRODUCTION

TECHNICAL FIELD

The present invention is concerned with the production of hydrogen and, more particularly, with the enhancement of hydrogen production in photosynthetic microorganisms with natural hydrogen production capability. In particular the invention relates to photosynthetic microorganisms, including cyanobacteria and algae that are able to produce hydrogen from water using a hydrogenase. The invention also relates to the manipulation of the physiology of such organisms in order to enhance hydrogen production.

BACKGROUND ART

The development of a clean, sustainable and economically viable energy supply for the future is one of the most urgent challenges of our generation. Oil production is expected to peak in around 5 to 30 years time and economically viable oil reserves will be largely depleted by 2050. More recent reports, however, suggest that oil production may already have peaked in 2000. A viable hydrogen economy requires clean, sustainable and economic ways of generating hydrogen. Current hydrogen production depends almost entirely on the use of non-renewable resources (i.e. steam reformation of natural gas, coal gasification and nuclear power driven electrolysis of water). Although these approaches are initially likely to drive a transition towards a hydrogen economy, the hydrogen produced is more expensive and contains less energy than the non-renewable energy source from which it is derived. In addition, the use of fossil fuels and nuclear power is unsustainable. Therefore, there is a clear need to establish economically viable means of hydrogen production.

A particularly desirable option is the production of hydrogen using photosynthetic organisms, since the ultimate energy source is solar energy. Algal pond technology is likely to be cheap compared to alternatives such as photovoltaic cells. Furthermore and in contrast to all other sustainable energy systems (except biomass), which incur an initial $CO_2$ emissions penalty during manufacture, algae have the advantage that they are able to sequester $CO_2$ while self-assembling their intricate solar collectors. This gives them an additional intrinsic value in terms of carbon trading upon setup.

Solar energy is captured and stored in the form of starch and other molecules including proteins, which are subsequently used as a fuel to drive ATP production via the processes of oxidative phosphorylation in the mitochondria (FIG. 1). Some green algae have evolved the ability to channel the $H^+$ and $e^-$ stored in starch into $H_2$ production under anaerobic conditions. Thus there is the promise that hydrogen may be generated using algal bioreactors. In the first step of photosynthesis, Photosystem II (PSII) drives the most highly oxidizing reaction known to occur in biology, splitting $H_2O$ into oxygen ($O_2$), protons ($H^+$) and electrons ($e^-$) (FIG. 1). $O_2$ is released into the atmosphere and is responsible for maintaining aerobic life on Earth. The derived $e^-$ are passed along the photosynthetic $e^-$ transport chain (FIG. 2) from PSII via Plastoquinone (PQ) to Cytochrome $b_6f$ (cyt $b_6f$) and Photosystem I (PSI), and are ultimately used in the production of NADPH. In a parallel process (photophosphorylation), $H^+$ are released into the thylakoid lumen (FIG. 1) where they generate a $H^+$ gradient that is used to drive ATP production via ATP synthase. NADPH and ATP are subsequently used to produce starch and other biomolecules.

ATP and NADPH/NADH are fundamental requirements of all living cells. The inhibition of PSII (eg. by incubation in the dark) blocks the supply of $H^+$ and $e^-$ that are used to generate ATP and NADPH via photophosphorylation in the chloroplast. For a time, the shortage of ATP and NADPH caused by the inhibition of PSII can be compensated for via aerobic respiration mediated by the mitochondrial $e^-$ transport chain (FIG. 1), which metabolises starch, proteins and lipids. As its name suggests, oxidative phosphorylation requires $O_2$. The $O_2$ is combined with $H^+$ and $e^-$ by mitochondrial Complex IV to generate $H_2O$, which essentially acts as an $H^+$ and $e^-$ sink (FIG. 1). Under anaerobic conditions Complex IV is inhibited, blocking $e^-$ transport through the remainder of the $e^-$ transport chain consisting of Complexes I, II, III and Cytochrome oxidase (also known as Complex IV). Under strictly anaerobic conditions most photosynthetic organisms die. However, a select number of photosynthetic organisms such as the green alga C. reinhardtii have a third mechanism, which allows them to switch into a mode of ATP and NADPH production (FIG. 2). Under illuminated anaerobic conditions, they generate ATP in the chloroplast while simultaneously producing $H_2$ as a volatile $H^+/e^-$ sink, instead of $H_2O$. This process involves the Hydrogenase HydA located in the chloroplast stroma (Florin et al., 2001 and Happe and Kaminski, 2002.). HydA transcription and activity is strongly inhibited by $O_2$ (Ghirardi et al., 1997). It is likely that oxygen sensitivity acts as a molecular control switch which tells HydA when anaerobic conditions occur.

In order to optimise ATP and NADPH production under transient light conditions, plants and algae developed a redox-controlled regulation mechanism called the LHC state transitions. This process normally balances PSI and PSII turnover rates by regulating the size of their light harvesting antennae (LHCI & LHCII, respectively), specifically by shuttling Lhcb proteins between the two photosystems (State 1: large PSII antenna; State 2: large PSI antenna). In the green alga C. reinhardtii, this process results in a switch from linear to cyclic photosynthetic electron transport, which could compete with the Fe-hydrogenase HydA for e− at the reducing side of PSI. Cells blocked in state 1 under anaerobic conditions do not perform cyclic electron transfer in which electrons are transferred back to Cytb6f. Under these conditions the Fe-hydrogenase HydA no longer has to compete with Cytb6f mediated cyclic electron transport for the electrons derived from PSI.

The earliest reports of algal $H_2$ production date back to the 1930s (Stephenson and Stickland, 1931). It was discovered that certain green algae and cyanobacteria could produce $H_2$ gas upon illumination, by a reaction that was extremely sensitive to inhibition by $O_2$. Despite the obvious attraction of using photosynthetic organisms for sustainable $H_2$ production from $H_2O$, it was not until 2000 that Melis and co-workers first reported a method to overcome this inhibition (Melis, 2000 and U.S. Patent Application No. 2001/005343). Melis describes a process in which the inhibition was lifted by temporally separating the $O_2$ generating $H_2O$ splitting reaction, catalysed by PSII, from the $O_2$ sensitive $H_2$ production catalysed by the chloroplast Hydrogenase (HydA). This separation was achieved by culturing C. reinhardtii first in the presence of sulfur to build stores of an endogenous substrate and then in the absence of sulfur. Sulfur is required for the de novo synthesis of the D1 protein of the PSII reaction centre, and of course of many other organic components of the cell. The D1 protein has an approximate half-life of 30 min, being damaged under non-optimal conditions through the highly oxidizing reaction that it drives. In the presence of sulfur, high levels of active PSII are maintained and $H_2O$ is split into $H^+$, $e^-$ and $O_2$. As sulfur levels decrease in a sulfur depleted medium the $H^+$ and $e^-$ are subsequently recombined by HydA to generate $H_2$, which lifts the inhibition of the Hydrogenase induced by $O_2$. This, for the first time, facilitated long-term $H_2$ production using wild type (WT) *C. reinhartii*.

The Melis process is, however, subject to considerable practical constraints. The actual rate of hydrogen gas accumulation is at best 15 to 20% of the photosynthetic capacity of the cells (Melis and Happe 2001) and suffers the inherent limitation that hydrogen production by S deprivation of the algae cannot be continued indefinitely. The yield begins to level off and decline after about 40-70 hours of S deprivation, and after about 100 hours of S deprivation the algae need to revert to a phase of normal photosynthesis to replenish endogenous substrates.

International Publication No. WO 03/067213 describes a process for hydrogen production using *Chlamydomonas reinhardtii* wherein the algae has been genetically modified to down regulate expression of a sulfate permease, Crcp-SulP, through insertion of an antisense sequence. This is said to render obsolete prior art sulfur deprivation techniques, as it obviates the need to physically remove sulfur nutrients from growth media in order to induce hydrogen production. The reduced sulfur uptake by the cell using this technique not only results in a substantial lowering of the levels of the major chloroplast proteins such as Rubisco, D1 and the LHCII, but also deprives the cell of sulfur for use in the biosynthesis of other proteins.

Consequently there remains a need to identify a sustainable and efficient process for photosynthetic hydrogen production that avoids sulfur deprivation.

SUMMARY OF THE INVENTION

The present invention is based upon the surprising observation that disruption of the regulation of the oxidative phosphorylation pathway in the mitochondria in the light affects the cell in a fashion which increases starch levels in the chloroplast, inhibits photosynthetic cyclic electron transfer and reduces oxygen production by PSII but permits linear electron transfer to PSI and Fd, and therefore allows operation of a Hydrogenase (HydA) that accepts electrons from PSI, with a reduction in the inherent oxygen inhibition.

Accordingly, a first aspect of the present invention provides a process for the production of hydrogen, comprising the steps of:

(i) providing a photosynthetic microorganism having electron transfer capability through a photosynthetic "light" reaction and through a respiratory electron transfer chain involving an oxidative phosphorylation pathway, and which expresses a hydrogenase, wherein regulation of the oxidative phosphorylation pathway is disrupted with the result that electron flow along the respiratory electron transfer chain toward cytochrome oxidase (complex IV) is reduced;

(ii) culturing the microorganism under microoxic and illuminated conditions; and (iii) collecting evolved hydrogen.

A number of organisms are physiologically suited to use in this process. In particular, photosynthetic microorganisms capable of using water as an indirect substrate for hydrogen production and which include a hydrogenase are used, and these include cyanobacteria and algae, particularly green algae but also blue-green algae such as those of *Synechococcus* sp. and red algae, more particularly the the *Chlorococcales* and *Volvocales* especially those of *Chlamydomonas* spp. (e.g. *Chlamydomonas reinhardtii, Chlamydomonas* MGA161), *Scenedesmus* spp, (eg. *Scenedesmus obliquus*) and, *Chlorococcum* spp. (eg. *Chlorococcum littorale*), *Chlorella* spp. (eg. *Chlorella fusca, Platymonas* spp.(eg. *Platymonas subcordisiformis*), *Trichomonas* spp. (eg. *Trichomonas vaginalis*). The alga *Chlamydomonas reinhardtii* is particularly preferred as processes for the genetic manipulation of the organism are well developed and its haploid genome has been sequenced.

Any suitable means of disrupting oxidative phosphorylation may be employed. In an embodiment the microorganism is one in which regulation of the oxidative phosphorylation pathway of the mitochondria is disrupted, through reduction or elimination of the activity of a nuclear-encoded mitochrondrial transcription termination factor which regulates oxidative phosphorylation such as in a moc1 knock out. Such a high hydrogen-producing mutant is *Chlamydomonas reinhardtii* Stm6. Stm6 has been shown to produce hydrogen at the rate 3.5 to 7 times that of the wild type under the conditions tested.

The rate of hydrogen production may be further increased by the addition of an uncoupler of ATP synthase from the photosynthetic electron transport chain such as carbonyl-cyanide m-chlorophenylhydrazone (CCCP), 1,3-Dicyclohexylcarbodiimide (DCC), Ammonium chloride, Venturicidin, carbonyl cyanide p-trifluoromethoxyphenylhydrazone (FCCP), 2,4-dinitrophenol, Gramicidin and Nigericin to achieve rates ~15 times of the wild type. Such uncouplers essentially increase the flow of $H^+$ from the thylakoid lumen to the stroma, where they become available as a substrate for HydA.

The microorganism described above may be cultured under illuminated conditions in order to expand biomass in either aerobic or anaerobic conditions in the presence of an external nutrient supply. In an embodiment, a waste stream is employed as a carbon source for this culture and so the waste stream becomes depleted in carbon, such as may be useful, for example, in treating the stream to remove an organic pollutant. Still further, the microorganism may be cultured under aerobic and illuminated conditions in order to expand the biomass, followed by the steps of i) gasifying the expanded biomass; and ii) collecting the hydrogen so-produced.

This provides an alternative to direct collection of hydrogen from the culture when illuminated under anaerobic conditions.

According to a further aspect of the present invention there is provided a photosynthetic microorganism having electron transfer capability through a photosynthetic "light" reaction and through a respiratory electron transfer chain involving an oxidative phosphorylation pathway, and which expresses a hydrogenase, wherein regulation of the oxidative phosphorylation pathway is disrupted with the result that electron flow along the respiratory electron transfer chain toward cytochrome oxidase (complex IV) is reduced.

In an embodiment the microorganism is a Moc1 knockout in an alga such as *Chlamydomonas reinhardtii*, in particular, *Chlamydomonas reinhardtii* Stm6 as deposited with the Culture Collection of Algae and Protozoa (CCAP) on 1 Jul. 2003 under CCAP accession number 11/129.

It will be clearly understood that, although a number of prior art publications are referred to herein, this reference does not constitute an admission that any of these documents forms part of the common general knowledge in the art, in Australia or in any other country.

For the purposes of this specification it will be clearly understood that the word "comprising" means "including but not limited to", and that the word "comprises" has a corresponding meaning.

B. Effect of light intensity on hydrogen production of wild type and Stm6 *Chlamydomonas reinhardtii* cultures estimated by gas mass spectrometry. $H_2$ evolution (relative rates) by WT and Stm6 cells (dark adapted for 30 min) during 1 minute periods of continuous illumination at different irradiance levels. Stm6 consistently showed 500-700% higher rates (as indicated by peak labels) of hydrogen production than the wild type.

C. The uncoupler CCCP stabilizes $H_2$ production rates at levels ~1500% higher than in the WT, as estimated by hydrogen Clark electrode measurements (UniSense). This indicates that HydA activity may be limited by the rate of substrate supply.

Figure 4:
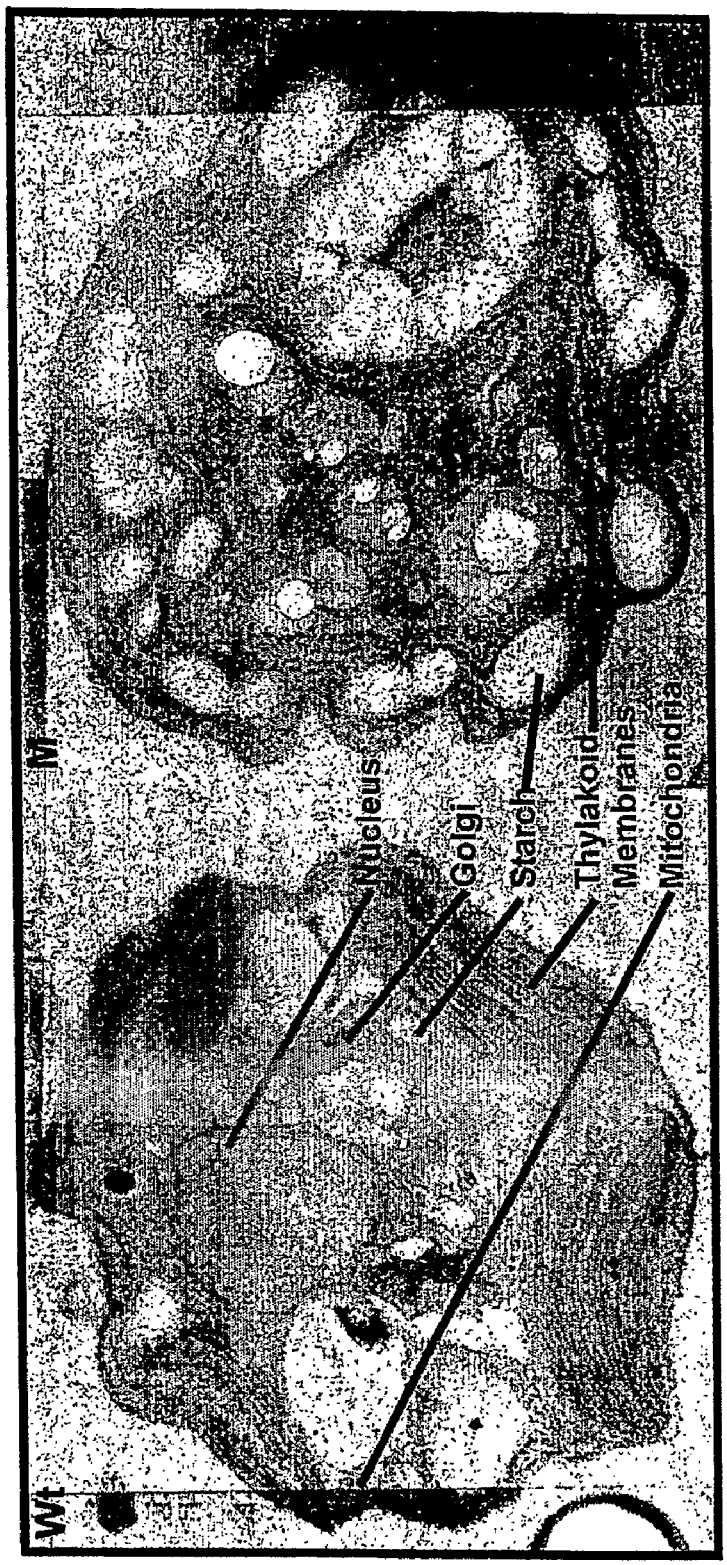

FIG. 4 shows electron micrographs of stained sections of WT and high $H_2$ producing mutant *C. rheinhardtii*. C-chloroplast, G-Golgi, M-Mitochondria, N-Nucleus, S-Starch. Note that: 1) the grana of the mutant are much less stacked than those of the WT. This has implications for the light capturing properties of the mutant. The mutant appears to have large carbohydrate stores in the form of starch. The $H^+$ and $e^-$ derived from water are stored in starch, before being converted to $H_2$ by HydA.

Figure 5:
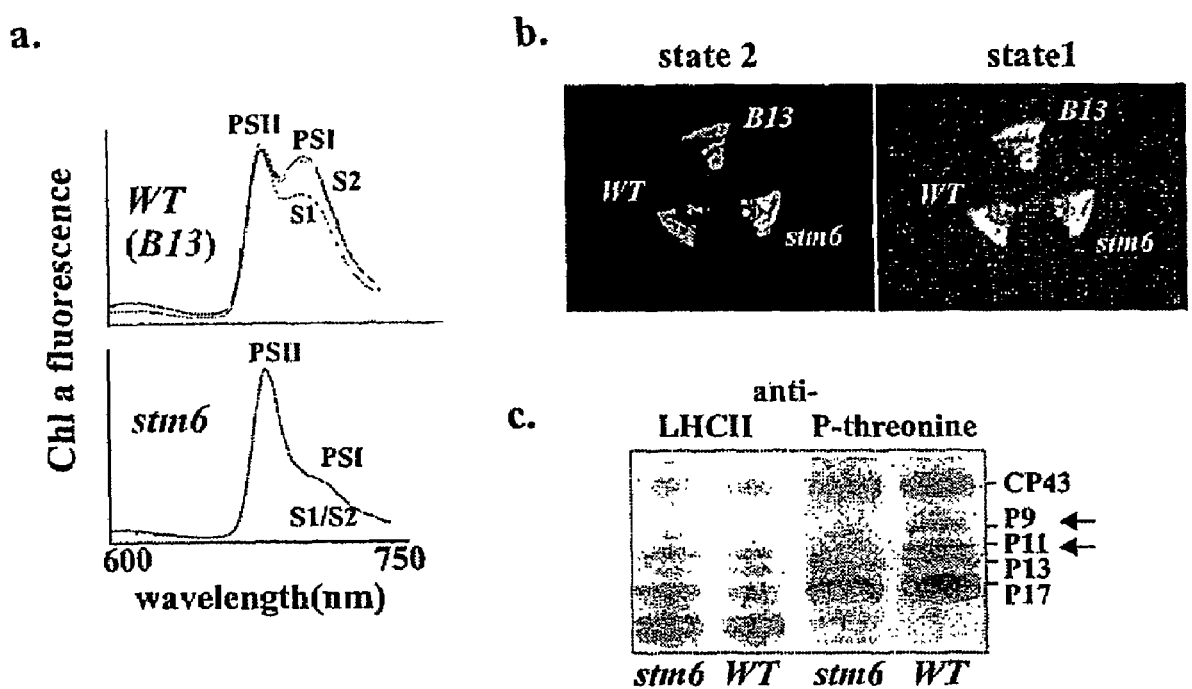
Figure 6:
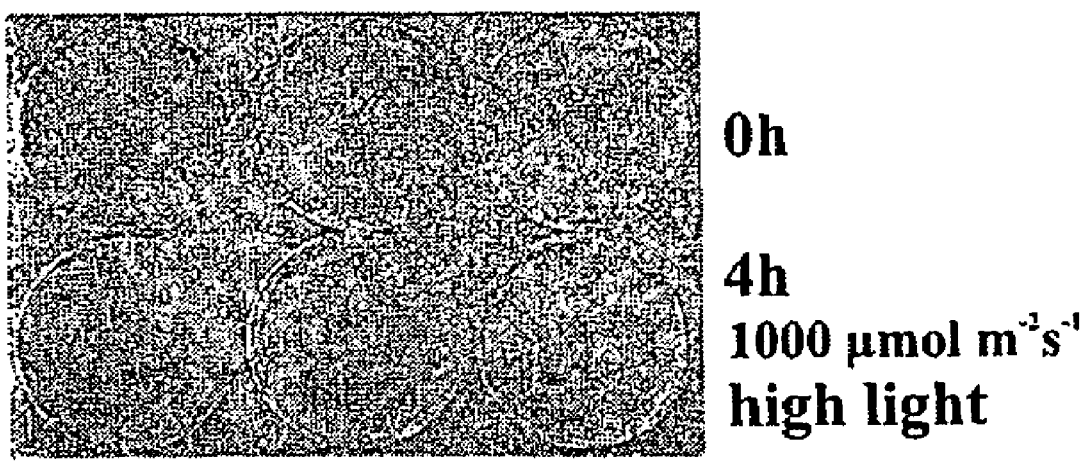
Figure 6:
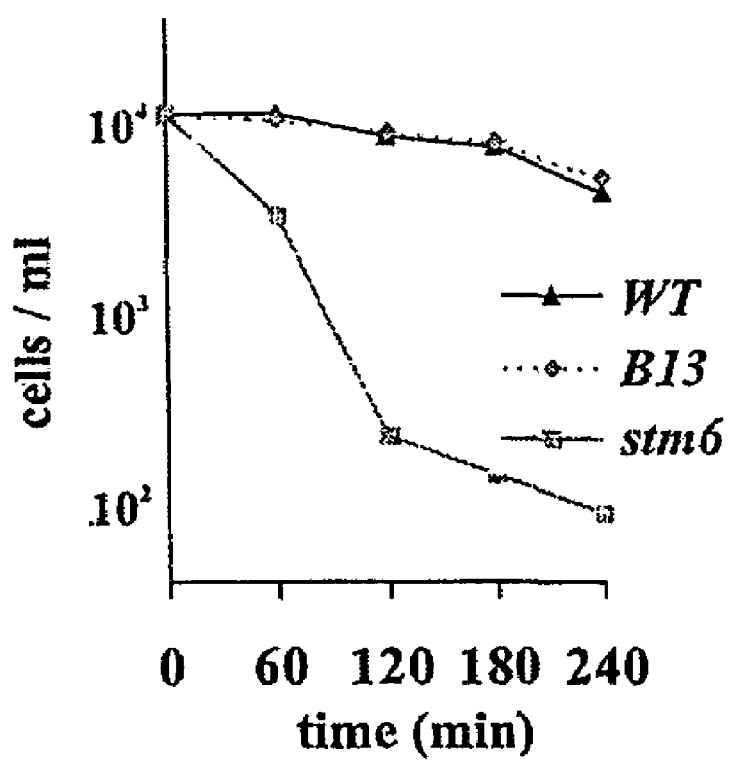

FIG. 5 provides an analysis of light-induced short-term adaptation mechanisms in the chloroplast:

a) State transitions analysed by 77 k fluorescence spectroscopy in WT, B13 and Stm6 b) Fluorescence video image of WT, B13 and Stm6 on TAP-agar plates in state 2 and state 1 (Illumination with actinic light at 620 nm±15 min illumination with 710 nm PSI light)

c) In vivo phosphorylation protein pattern of thylakoid membranes isolated from state2-adapted WT and Stm6 cell FIG. 6 shows that Stm6 is sensitive to light stress:

a) WT, B13 and Stm6 strains, cultivated to their mid logarithmic growth phase in TAP medium, exposed to 1000 µmol $m^{-2}$ $s^{-1}$ white light for 4 hours, subsequently inoculated on TAP agar plates and grown for 7 days in 40 µmol $m^{-2}s^{-1}$ white light.

b) High light cell rates surviving high light treatment over a period of 4 hours in WT, B13 and Stm6 strains. Cells were diluted to $1\times10^4$ cells/ml prior to light treatment.

Figure 7:
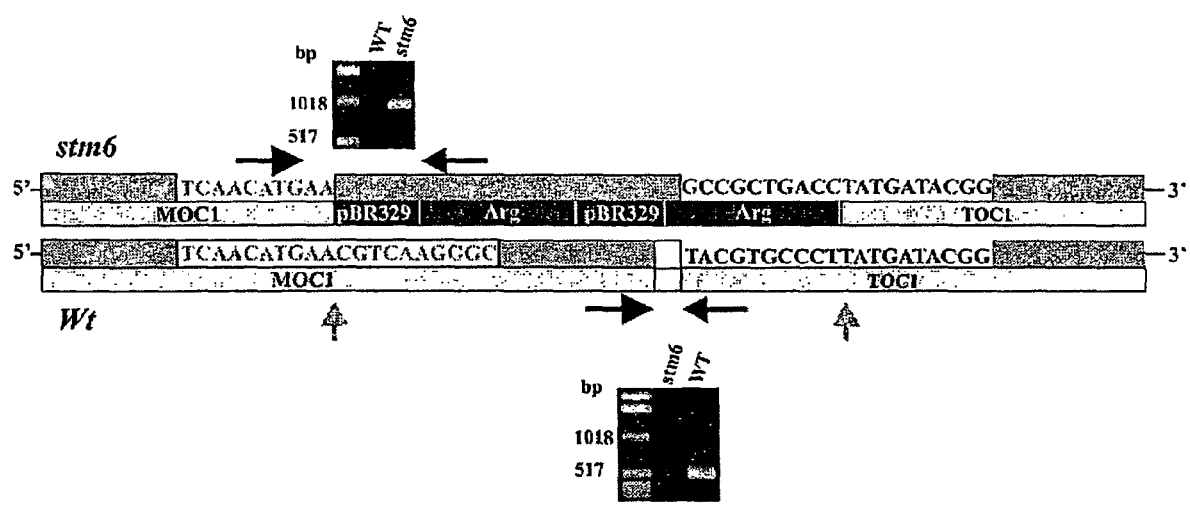

FIG. 7 illustrates the genomic DNA site in Stm6 affected by the tandem nuclear insertion of two pArg7.8 plasmids:
    by sequence analysis after chromosome walking LMS-PCR) and:
    by PCR analysis with specific moc1, toc1 and pArg7.8 primers.

The 2 black arrow sets mark the primer pairs used for PCR.

The 2 grey arrows mark the integration sites of the nuclear insertion in WT.

Figure 8:
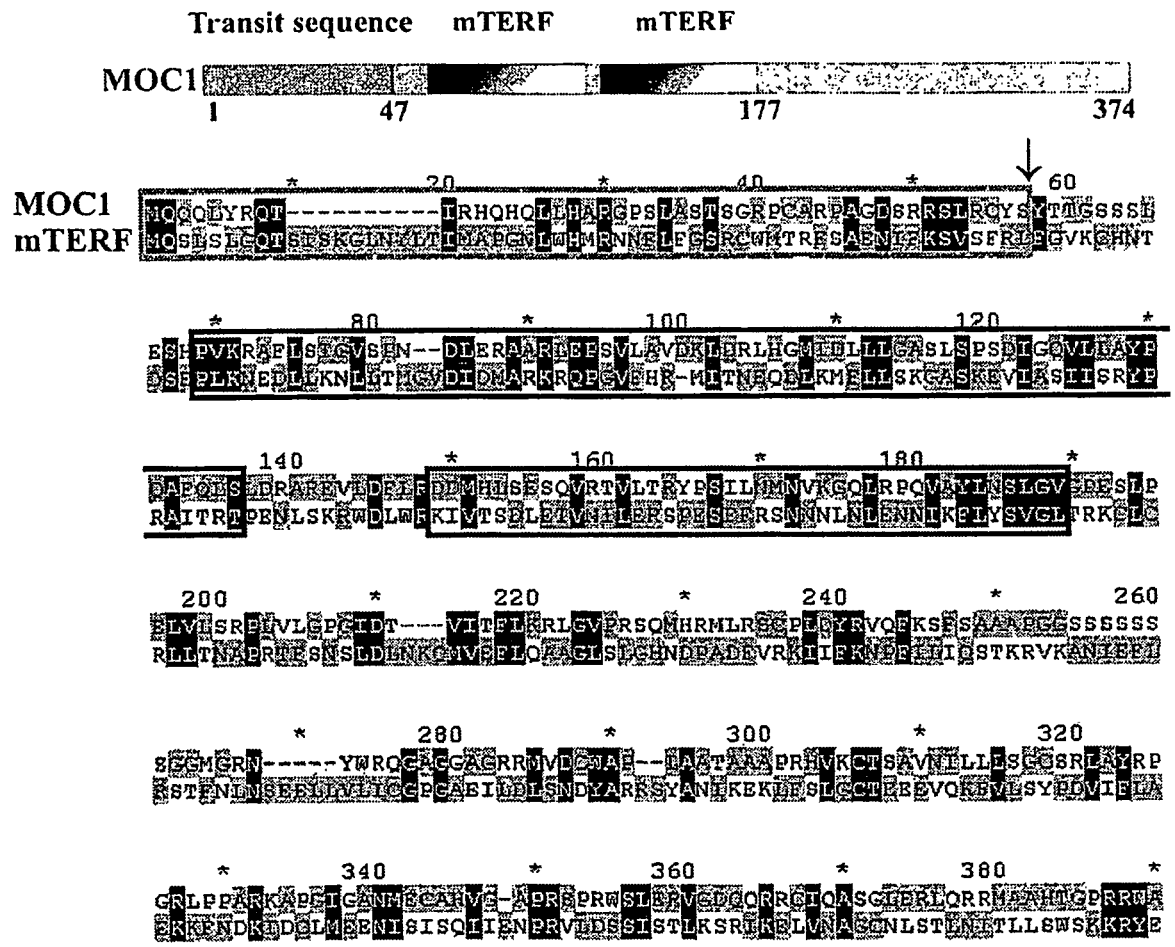

FIG. 8 gives the protein sequence of MOC1 and alignment with the human transcription termination factor mTERF. The model and the boxes mark the locations of the mitochondrial transit sequences and the identified mTERF domain structures in MOC1.

Figure 9:
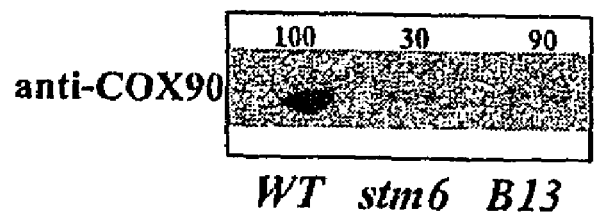
Figure 9:
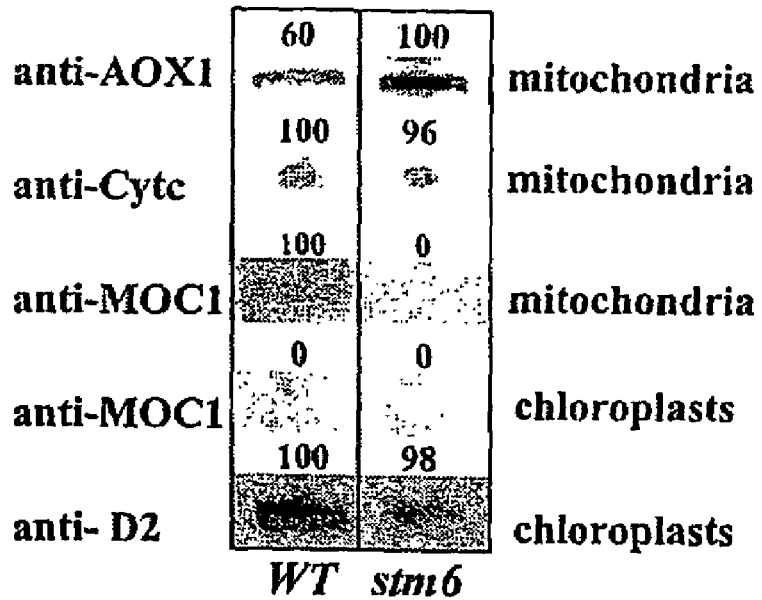
Figure 9:
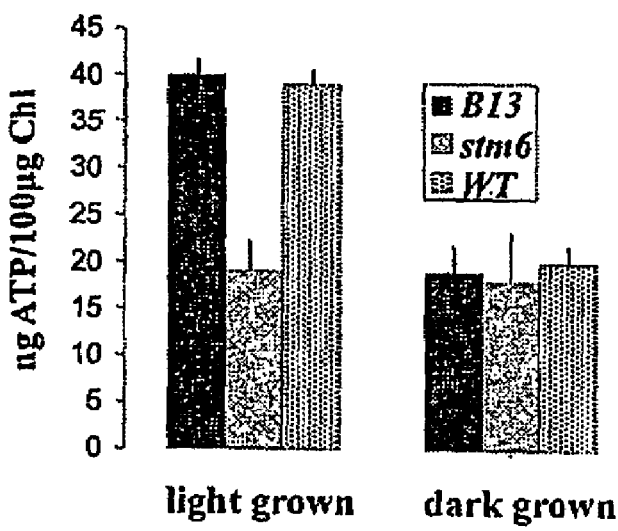

FIG. 9 is a western analysis and ATP level measurements in WT, Stm6 and B13:

a) immunoblot of light grown cells using antibodies specific for cytochrome oxidase subunit COX90 b) immunoblot using anti-peptide antibodies to demonstrate localisation of MOC1 to the mitochondrion and not the chloroplasts (anti-D2 and anti-Cyt c blots were performed as controls for chloroplasts and mitochondria, respectively) and to demonstrate up-regulation of AOX1 in Stm6. Relative intensities of cross-reactions, as determined by densitometry, are indicated.

c) ATP levels in cells of WT, Stm6 and B13 grown in the light and dark.

Figure 10:
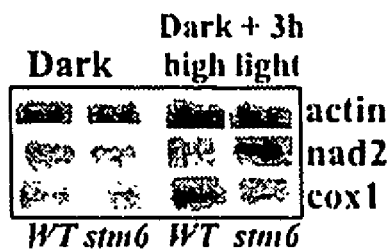
Figure 10:
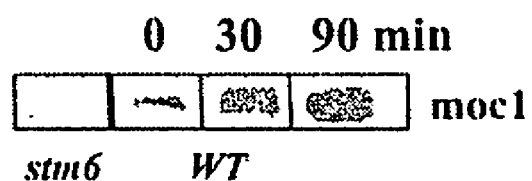
Figure 10:
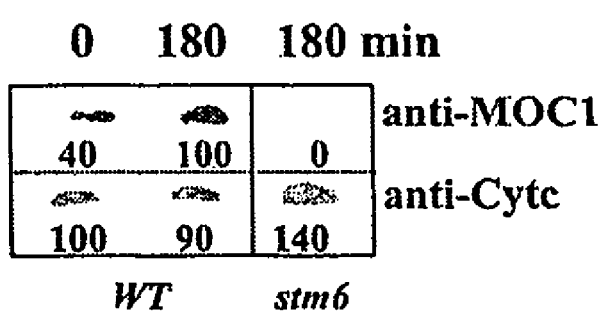
Figure 10:
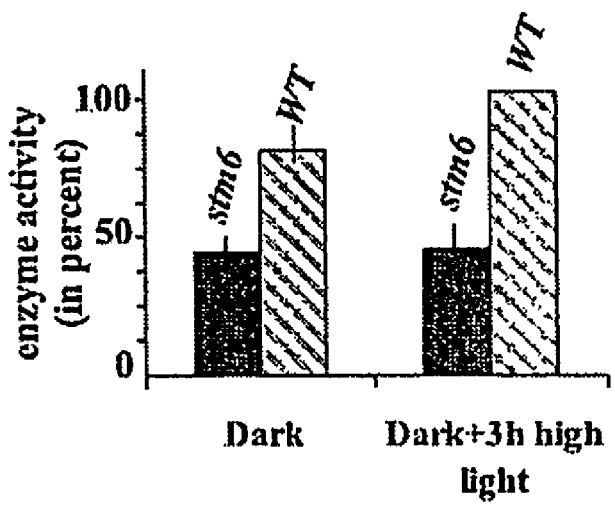

FIG. 10 shows evidence for the role of MOC1 in light-induced mitochondrial transcription regulation:

a) Semi-quantitative RT-PCR of nad2 and cox1 in dark-grown cultures and after exposure to light (3 hours 200 µmol $m^{-2}s^{-1}$); mRNA levels were normalised to that of actin.

b) moc1-Northern Blots of isolated total RNA from dark- and light-grown WT.

c) anti-MOC1 and anti-cytochrome immunoblots of mitochondria isolated from WT cells exposed to high light (800 µmol $m^{-2}$ $s^{-1}$) for 0 and 180 min. The Stm6 blot was performed as a control.

d) Cytochrome oxidase activity measurements in isolated mitochondria from WT and Stm6 (3 hours 200 µmol $m^{-2}s^{-1}$).

Figure 11:
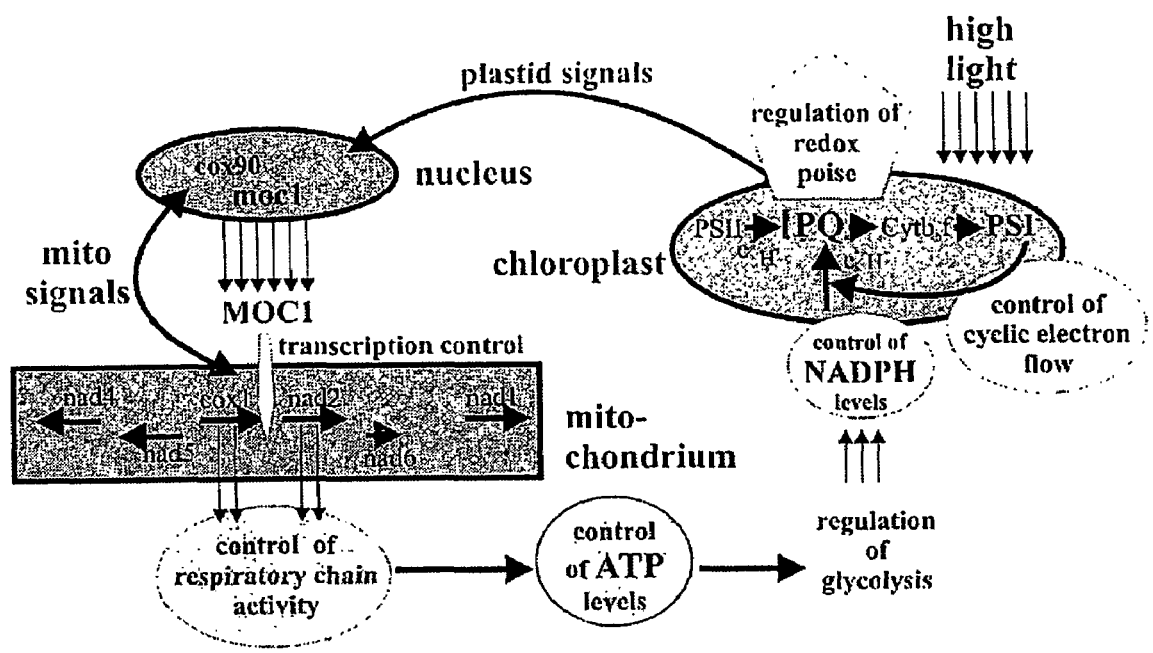

FIG. 11 is an illustration of a model describing the role of MOC1 in the regulation of mitochondrial respiratory electron transport upon high light stress and its influence on light-induced redox control processes in the chloroplast. Grey boxes represent organelles.

Figure 12:
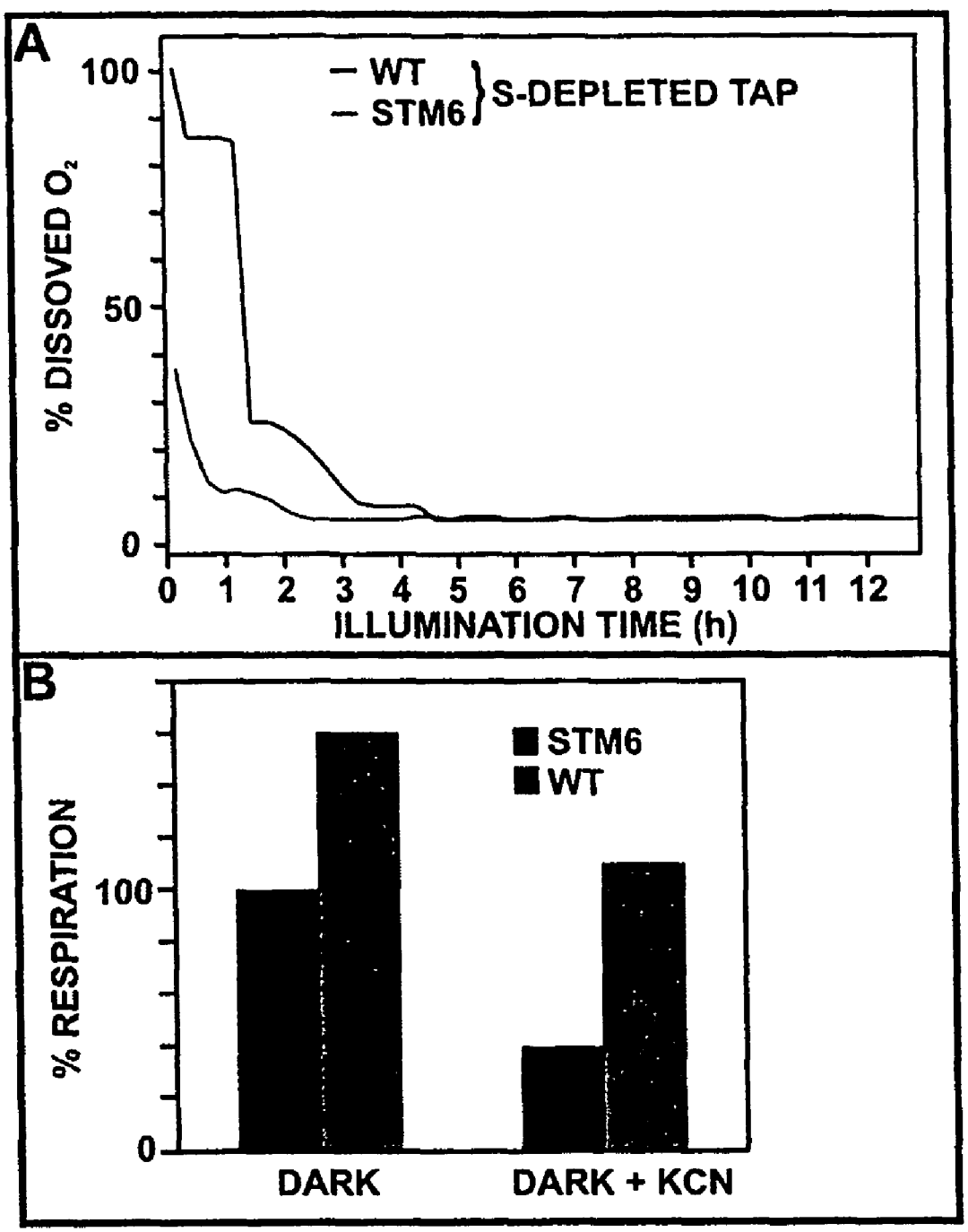

FIG. 12 shows dissolved oxygen concentration measurements:

Panel A: Cell cultures were grown in sulfur replete TAP medium under constant illumination and transferred at time=0 to sulfur-depleted TAP medium.

Panel B: Cellular respiration measurements were conducted in the dark using light cultivated cell preparations (30 µg Chl/ml)±5 mM KCN.

Figure 13:
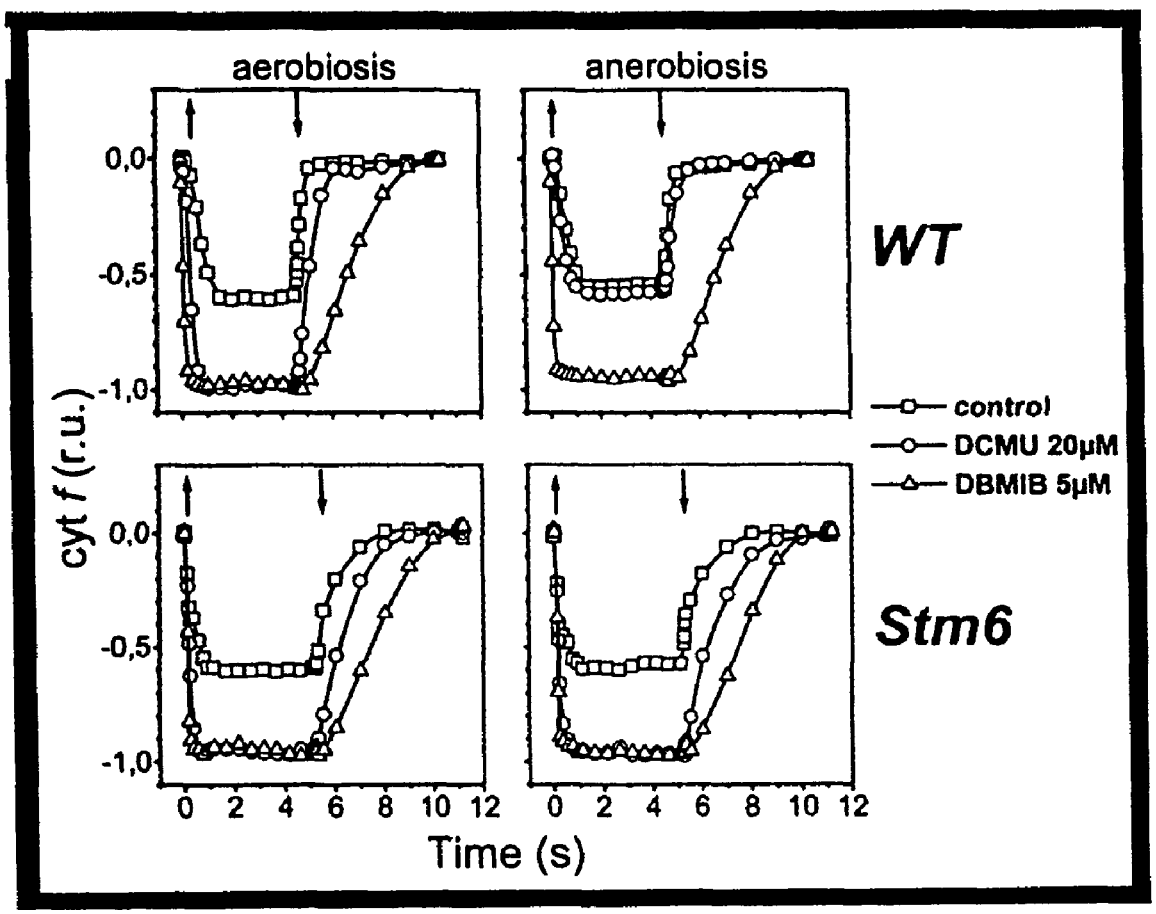

FIG. 13 is a graph showing spectroscopic determination of cyclic electron transport through measuring the light induced redox changes of cyt f in the presence of either 20 µM dichlorophenyl dimethyl urea (DCMU: inhibits e$^-$ transport from PSII to cytb$_6$f) or 5 µM 2,5-dibromo-6-isopropyl-3-methyl-1,4-benzoquinone: Up arrow: light on. Down arrow: light off. Absorbance decrease corresponds to oxidation of cyt f.

Figure 14:
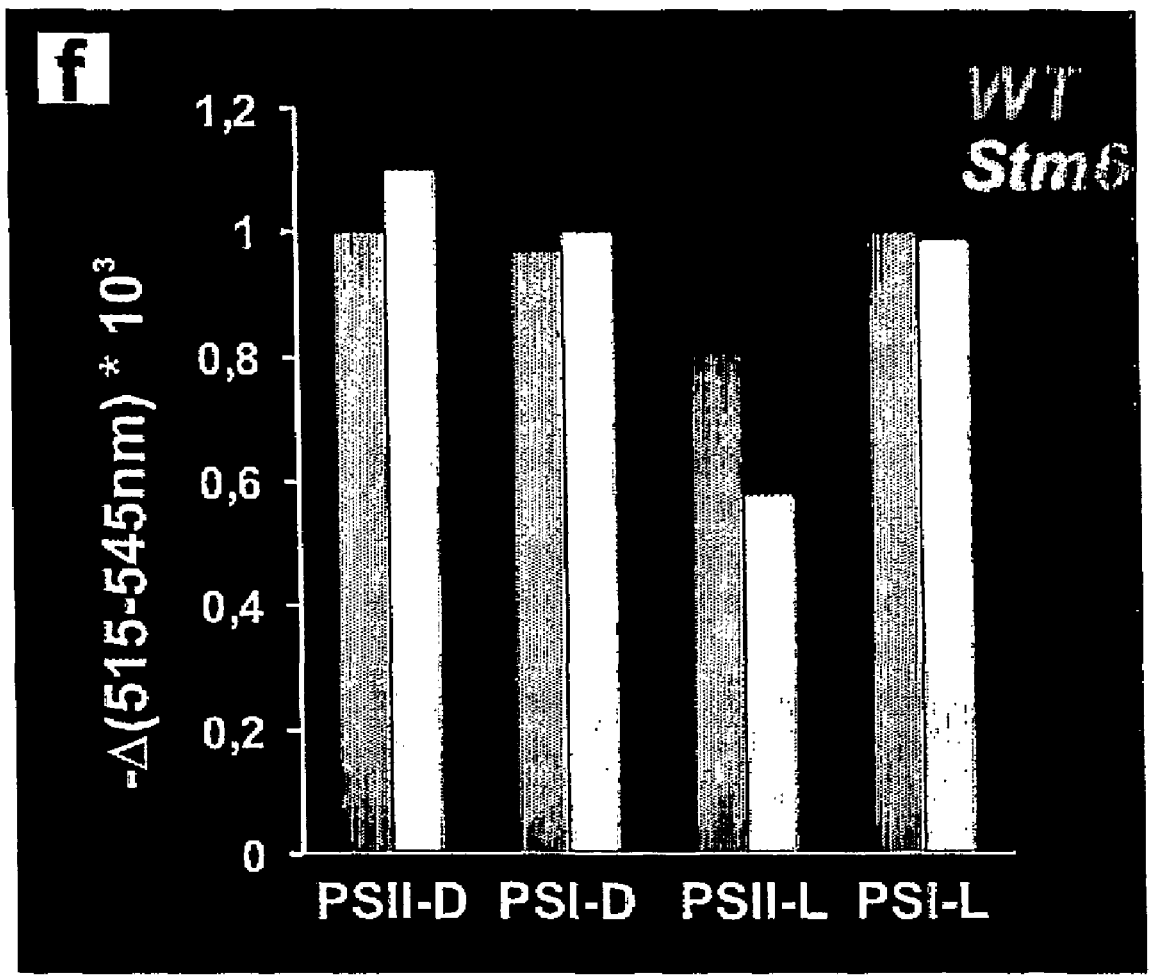

FIG. 14 is a graph showing PSII and PSI activity levels in WT *Chlamydomonas reinhardtii* and Stm6.

Figure 15:
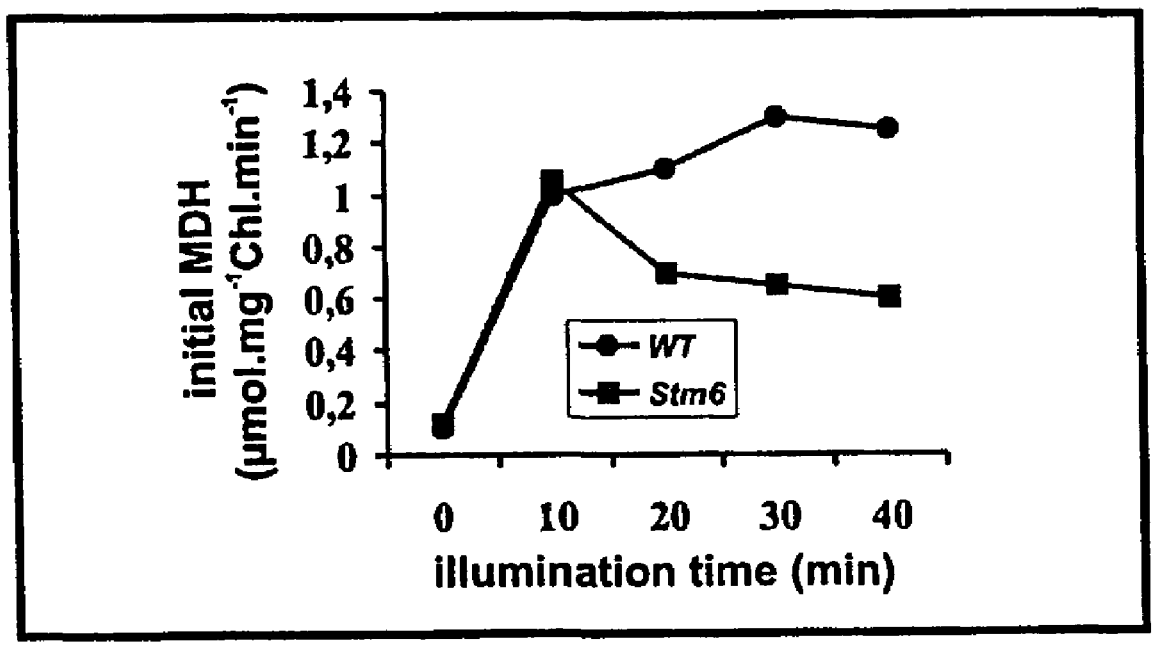

FIG. 15 is a graph showing Malate NADPH-dehydrogenase activity measurements in WT *Chlamydomonas reinhardtii* and Stm6 cell cultures.

Figure 16:
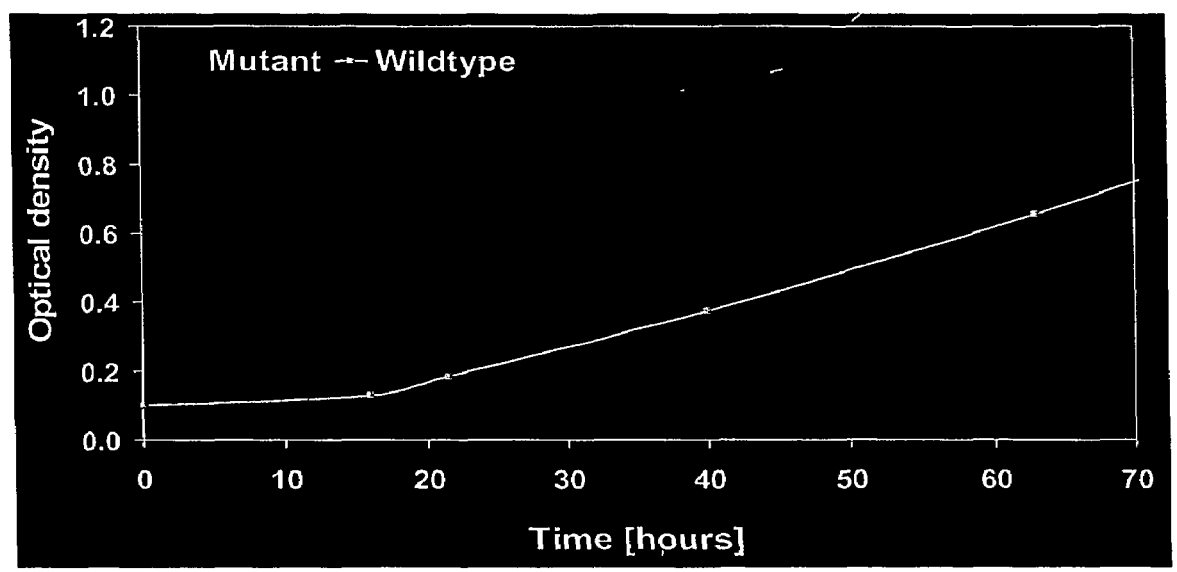

FIG. 16 gives a comparison of growth rates of Stm6 and wild type *Chlamydomonas reinhardtii* under low light levels.

DETAILED DESCRIPTION OF THE INVENTION

The invention will now be described in detail by way of reference only to the following non-limiting examples and drawings.

In seeking to identify cellular components important for the redox-controlled regulation of photosynthesis the approach was to screen for mutants that are perturbed in state transitions. This is a redox-controlled mechanism that balances the excitation of the two photosynthetic reaction centres involved in electron flow, between photosystems I and II (Bonaventura and Myers, 1969; Murata, 1969). When the plastoquinone pool, which is a component of the photosynthetic electron transport chain linking PSII and PSI, becomes too reduced, mobile light-harvesting antennae detach from PSII, following redox-activated phosphorylation and dock with PSI thus increasing the excitation of PSI and making the PQ pool more oxidized (into so-called state 2). The reverse process occurs when the PQ becomes more oxidised (to achieve state 1) (Allen et al., 1981; Horton et al., 1981). A rapid chlorophyll-fluorescence based screen was employed to identify colonies of the model organism, the green alga *Chlamydomonas reinhardtii,* that are blocked in state transitions (the inter conversion of state 1 and state 2) (Kruse et al., 1999; Fleichmann et al., 1999). A gene that is important for state transitions was identified. Surprisingly the gene product was found to be a nuclear encoded protein targeted to the mitochondrion not the chloroplast and is involved in regulating mitochondrial gene expression.

The term "isolated" is used herein in reference to purified polynucleotide or polypeptide molecules. As used herein, "purified" refers to a polynucleotide or polypeptide molecule separated from substantially all other molecules normally associated with it in its native state. More preferably, a substantially purified molecule is the predominant species present in a preparation. A substantially purified molecule may be greater than 60% free, preferably 75% free, more preferably 90% free, and most preferably 95% free from the other molecules (exclusive of solvent) present in the natural mixture. The term "isolated" is also used herein in reference to polynucleotide molecules that are separated from nucleic acids that normally flank the polynucleotide in nature. Thus, polynucleotides fused to regulatory or coding sequences with which they are not normally associated, for example as the result of recombinant techniques, are considered isolated herein. Such molecules are considered isolated even when present, for example in the chromosome of a host cell, or in a nucleic acid solution. The terms "isolated" and "purified" as used herein are not intended to encompass molecules present in their native state.

"Wild type", as used herein, refers to a microorganism that has not been genetically modified to knock out or overexpress one or more of the presently disclosed transcription factors. Wild-type organisms may be used as controls to compare levels of expression and the extent and nature of trait modification with organism in which transcription is altered or ectopically expressed, e.g., in that it has been knocked out or overexpressed.

As used herein "sequence identity" refers to the extent to which two optimally aligned polynucleotide or peptide sequences are invariant throughout a window of alignment of components, e.g. nucleotides or amino acids. An "identity fraction" for aligned segments of a test sequence and a reference sequence is the number of identical components which are shared by the two aligned sequences divided by the total number of components in the reference sequence segment, i.e. the entire reference sequence or a smaller defined part of the reference sequence. "Percent identity" is the identity fraction times 100. Comparison of sequences to determine percent identity can be accomplished by a number of well-known methods, including for example by using mathematical algorithms, such as those in the BLAST suite of sequence analysis programs.

As used herein "suppression" or "disruption" of regulation refers to reduced activity of regulatory proteins, and such reduced activity can be achieved by a variety of mechanisms including antisense, mutation knockout or RNAi. Antisense RNA will reduce the level of expressed protein resulting in reduced protein activity as compared to wild type activity levels. A mutation in the gene encoding a protein may reduce the level of expressed protein and/or interfere with the function of expressed protein to cause reduced protein activity.

As used herein, the term "polypeptide" means an unbranched chain of amino acid residues that are covalently linked by an amide linkage between the carboxyl group of one amino acid and the amino group of another. The term polypeptide can encompass whole proteins (i.e. a functional protein encoded by a particular gene), as well as fragments of proteins. The term "protein" also includes molecules consisting of one or more polypeptide chains. Thus, a polypeptide of the present invention may also constitute an entire gene product, but only a portion of a functional, oligomeric protein having multiple polypeptide chains.

The terms "polynucleotide", "polynucleotide sequence", "nucleic acid sequence", "nucleic acid fragment", and "isolated nucleic acid fragment" are used interchangeably herein. These terms encompass nucleotide sequences and the like. A polynucleotide may be a polymer of RNA or DNA that is single- or double-stranded, that optionally contains synthetic, non-natural or altered nucleotide bases. A polynucleotide in the form of a polymer of DNA may be comprised of one or more segments of cDNA, genomic DNA, synthetic DNA, or mixtures thereof.

Nucleotides (usually found in their 5'-monophosphate form) are referred to by a single letter designation as follows: "A" for adenylate or deoxyadenylate (for RNA or DNA, respectively), "C" for cytidylate or deoxycytidylate, "G" for guanylate or deoxyguanylate, "U" for uridylate, "T" for deoxythymidylate, "R" for purines (A or G), "Y" for pyrimidines (C or T), "K" for G or T, "H" for A or C or T, "I" for inosine, and "N" for any nucleotide.

The terms "subfragment that is functionally equivalent" and "functionally equivalent subfragment" are used interchangeably herein. These terms refer to a portion or subsequence of an isolated nucleic acid fragment in which the ability to alter gene expression or produce a certain phenotype is retained whether or not the fragment or subfragment encodes an active enzyme. For example, the fragment or subfragment can be used in the design of chimeric genes to produce the desired phenotype in a transformed algae. Chimeric genes can be designed for use in suppression by linking a nucleic acid fragment or subfragment thereof, whether or not it encodes an active enzyme, in the sense or antisense orientation relative to a plant promoter sequence.

The terms "homology", "homologous", "substantially similar" and "corresponding substantially" are used interchangeably herein. They refer to nucleic acid fragments wherein changes in one or more nucleotide bases do not affect the ability of the nucleic acid fragment to mediate gene expression or produce a certain phenotype. These terms also refer to modifications of the nucleic acid fragments of the instant invention such as deletion or insertion of one or more nucleotides that do not substantially alter the functional properties of the resulting nucleic acid fragment relative to the initial, unmodified fragment. It is therefore understood, as those skilled in the art will appreciate, that the invention encompasses more than the specific exemplary sequences.

Moreover, the person skilled in the art recognizes that substantially similar nucleic acid sequences encompassed by this invention are also defined by their ability to hybridize, under moderately stringent conditions (for example, 0.5× SSC, 0.1% SDS, 60° C.) with the sequences exemplified herein, or to any portion of the nucleotide sequences disclosed herein and which are functionally equivalent to any of the nucleic acid sequences disclosed herein. Stringency conditions can be adjusted to screen for moderately similar fragments, such as homologous sequences from distantly related organisms, to highly similar fragments, such as genes that duplicate functional enzymes from closely related organisms. Post-hybridization washes determine stringency conditions. One set of preferred conditions involves a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. A more preferred set of stringent conditions involves the use of higher temperatures in which the washes are identical to those above except for the temperature of the final two 30 min washes in 0.2×SSC, 0.5% SDS was increased to 60° C. Another preferred set of highly stringent conditions involves the use of two final washes in 0.1×SSC, 0.1% SDS at 65° C.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature.

"Coding sequence" refers to a DNA sequence that codes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence.

Regulatory sequences may include, but are not limited to, promoters, translation leader sequences, introns, and polyadenylation recognition sequences.

"Promoter" refers to a DNA sequence capable of controlling the expression of a coding sequence or functional RNA. The promoter sequence consists of proximal and more distal upstream elements, the latter elements often referred to as enhancers. Accordingly, an "enhancer" is a DNA sequence that can stimulate promoter activity, and may be an innate element of the promoter or a heterologous element inserted to enhance the level or tissue-specificity of a promoter. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental conditions. It is further recognized that since in most cases the exact boundaries of regulatory sequences have not been completely defined, DNA fragments of some variation may have identical promoter activity. Promoters that cause a gene to be expressed in most cell types at most times are commonly referred to as "constitutive promoters".

The "translation leader sequence" refers to a polynucleotide sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences have been described (Turner, R. and Foster, G. D. (1995) Mol. Biotechnol. 3:225-236).

The "3' non-coding sequences" refer to DNA sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht, I. L., et al. (1989) Plant Cell 1:671-680.

"RNA transcript" refers to the product resulting from RNA polymerase-catalyzed transcription of a DNA sequence. When the RNA transcript is a perfect complementary copy of the DNA sequence, it is referred to as the primary transcript. An RNA transcript is referred to as the mature RNA when it is an RNA sequence derived from post-transcriptional processing of the primary transcript. "Messenger RNA (mRNA)" refers to the RNA that is without introns and that can be translated into protein by the cell. "cDNA" refers to a DNA that is complementary to and synthesized from a mRNA template using the enzyme reverse transcriptase. The CDNA can be single-stranded or converted into the double-stranded form using the Klenow fragment of DNA polymerase I. "Sense" RNA refers to RNA transcript that includes the mRNA and can be translated into protein within a cell or in vitro. "Antisense RNA" refers to an RNA transcript that is complementary to all or part of a target primary transcript or mRNA, and that blocks the expression of a target gene (U.S. Pat. No. 5,107,065). The complementarity of an antisense RNA may be with any part of the specific gene transcript, i.e., at the 5' non-coding sequence, 3' non-coding sequence, introns, or the coding sequence. "Functional RNA" refers to antisense RNA, ribozyme RNA, or other RNA that may not be translated but yet has an effect on cellular processes. The terms "complement" and "reverse complement" are used interchangeably herein with respect to mRNA transcripts, and are meant to define the antisense RNA of the message.

The term "operably linked" refers to the association of nucleic acid sequences on a single nucleic acid fragment so that the function of one is regulated by the other. For example, a promoter is operably linked with a coding sequence when it is capable of regulating the expression of that coding sequence (i.e., that the coding sequence is under the transcriptional control of the promoter). Coding sequences can be operably linked to regulatory sequences in a sense or antisense orientation. In another example, the complementary RNA regions of the invention can be operably linked, either directly or indirectly, 5' to the target mRNA, or 3' to the target mRNA, or within the target mRNA, or a first complementary region is 5' and its complement is 3' to the target mRNA.

Standard recombinant DNA and molecular cloning techniques used herein are well known in the art and are described more fully in Sambrook, J., Fritsch, E. F, and Maniatis, T. Molecular Cloning: A Laboratory Manual; Cold Spring Harbor Laboratory Press: Cold Spring Harbor, 1989. Transformation methods are well known to those skilled in the art and are described below.

The term "recombinant" refers to an artificial combination of two otherwise separated segments of sequence, e.g., by chemical synthesis or by the manipulation of isolated segments of nucleic acids by genetic engineering techniques.

The terms "recombinant construct", "expression construct", "chimeric construct", "construct", and "recombinant DNA construct" are used interchangeably herein. A recombinant construct comprises an artificial combination of nucleic acid fragments, e.g., regulatory and coding sequences that are not found together in nature. For example, a chimeric construct may comprise regulatory sequences and coding sequences that are derived from different sources, or regulatory sequences and coding sequences derived from the same source, but arranged in a manner different than that found in nature. Such construct may be used by itself or may be used in conjunction with a vector. If a vector is used then the choice of vector is dependent upon the method that will be used to transform host cells as is well known to those skilled in the art. For example, a plasmid vector can be used. The skilled artisan is well aware of the genetic elements that must be present on the vector in order to successfully transform, select and propagate host cells comprising any of the isolated nucleic acid fragments of the invention. The skilled artisan will also recognize that different independent transformation events will result in different levels and patterns of expression (Jones et al., (1985) EMBO J. 4:2411-2418; De Almeida et al., (1989) Mol. Gen. Genetics 218:78-86), and thus that multiple events must be screened in order to obtain lines displaying the desired expression level and pattern. Such screening may be accomplished by Southern analysis of DNA, Northern analysis of mRNA expression, immunoblotting analysis of protein expression, or phenotypic analysis, among others. The term "expression", as used herein, refers to the production of a functional end-product e.g., a mRNA or a protein (precursor or mature).

"Mature" protein refers to a post-translationally processed polypeptide; i.e., one from which any pre- or propeptides present in the primary translation product have been removed. "Precursor" protein refers to the primary product of translation of mRNA; i.e., with pre- and propeptides still present. Pre- and propeptides may be but are not limited to intracellular localization signals.

"Stable transformation" refers to the transfer of a nucleic acid fragment into a genome of a host organism, including both nuclear and organellar genomes, resulting in genetically stable inheritance. In contrast, "transient transformation" refers to the transfer of a nucleic acid fragment into the nucleus, or DNA-containing organelle, of a host organism resulting in gene expression without integration or stable inheritance. Host organisms containing the transformed nucleic acid fragments are referred to as "transgenic" organisms.

"Antisense inhibition" refers to the production of antisense RNA transcripts capable of suppressing the expression of the target protein. "Co-suppression" refers to the production of sense RNA transcripts capable of suppressing the expression of identical or substantially similar foreign or endogenous genes (U.S. Pat. No. 5,231,020). Co-suppression constructs in plants previously have been designed by focusing on overexpression of a nucleic acid sequence having homology to an endogenous mRNA, in the sense orientation, which results in the reduction of all RNA having homology to the overexpressed sequence (see Vaucheret et al. (1998) Plant J. 16:651-659; and Gura (2000) Nature 404:804-808). The overall efficiency of this phenomenon is low, and the extent of the RNA reduction is widely variable. Recent work has described the use of "hairpin" structures that incorporate all, or part, of an mRNA encoding sequence in a complementary orientation that results in a potential "stem-loop" structure for the expressed RNA. This increases the frequency of co-suppression in the recovered transgenic plants. Hairpin structures may contain the target RNA forming either the stem or the loop of the hairpin. Another variation describes the use of plant viral sequences to direct the suppression, or "silencing", of proximal mRNA encoding sequences (WO 98/36083). Both of these co-suppressing phenomena have not been elucidated mechanistically, although genetic evidence has begun to unravel this complex situation (Elmayan et al. (1998) Plant Cell 10:1747-1757).

The polynucleotide sequences used for suppression do not necessarily have to be 100% complementary to the polynucleotide sequences found in the gene to be suppressed. Polynucleotides that are at least 75% identical to a region of the polynucleotide that is target for suppression have been shown to be effective in suppressing the desired target. The polynucleotide should be at least 80% identical, preferably at least 90% identical, most preferably at least 95% identical, or the polynucleotide may be 100% identical to the desired target.

In an embodiment, antisense molecules are used to downregulate expression of nuclear genes regulating the activities of the mitochondria in cells such as moc1. The antisense reagent may be antisense oligodeoxynucleotides (ODN), particularly synthetic ODN having chemical modifications from native nucleic acids, or nucleic acid constructs that express such antisense molecules as RNA. The antisense sequence is complementary to the mRNA of the targeted gene, and inhibits expression of the targeted gene products. Antisense molecules inhibit gene expression through various mechanisms, e.g., by reducing the amount of mRNA available for translation, through activation of. RNAse H, or steric hindrance. One or a combination of antisense molecules may be administered, where a combination may comprise two or more different sequences.

Antisense molecules may be produced by expression of all or a part of the target gene sequence in an appropriate vector, where the transcriptional initiation is oriented such that an antisense strand is produced as an RNA molecule. Alternatively, the antisense molecule is a synthetic oligonucleotide. Preferred sequence length is 10 to 3000 nucleotides. More preferred sequence length is 100-2000 nucleotides. Even more preferred sequence length is 600 to 1200 nucleotides. The most preferred sequence length is 800-1000 nucleotides. The length is governed by efficiency of inhibition, specificity, including absence of cross-reactivity, and the like. However, it has also been found that short oligonucleotides, of from 7 to 8 bases in length, can be strong and selective inhibitors of gene expression (see Wagner et al. (1996) Nature Biotechnol. 14:840-844).

A specific region or regions of the endogenous sense strand mRNA sequence is chosen to be complementary to the antisense sequence based upon the gene sequence set forth, for example for moc1 under Genbank Accession No. AF53142. Selection of a specific sequence for the oligonucleotide may use an empirical method, where several candidate sequences are assayed for inhibition of expression of the target gene in an in vivo model. A combination of sequences may also be used, where several regions of the mRNA sequence are selected for antisense complementation.

Antisense oligonucleotides may be chemically synthesized by methods known in the art (see Wagner et al. (1993) supra.) Preferred oligonucleotides are chemically modified from the native phosphodiester structure, in order to increase their intracellular stability and binding affinity.

The nucleic acid compositions of the subject invention may encode all or a part of the target polypeptide. Double or single stranded fragments of the DNA sequence may be obtained by chemically synthesizing oligonucleotides in accordance with conventional methods, by restriction enzyme digestion, by PCR amplification, etc. For the most part, DNA fragments will be at least 25 nt, usually at least 50 nt or 75 nt or 100 nt but may be as long as 200 nt, 240 nt, 270 nt, 300 nt, and even as long as 400 nt. Small DNA fragments are useful as primers for PCR, hybridization screening probes, etc. For use in amplification reactions, such as PCR, a pair of primers will be used. The exact composition of the primer sequences is not critical to the invention, but for most applications the primers will hybridize to the subject sequence under stringent conditions, as known in the art. It is preferable to choose a pair of primers that will generate an amplification product of at least about 50 nt, preferably at least about 100 nt. Algorithms for the selection of primer sequences are generally known, and are available in commercial software packages. Amplification primers hybridize to complementary strands of DNA, and will prime towards each other.

The sequence of a nucleic acid or gene, including any flanking promoter regions and coding regions, may be mutated in various ways known in the art to generate targeted changes in promoter strength, sequence of the encoded protein, etc. The DNA sequence or protein product of such a mutation will usually be substantially similar to the sequences provided herein, i.e., will differ by at least one amino acid, and may differ by at least one or two but not more than about ten amino acids. The sequence changes may be substitutions, insertions or deletions. Deletions may further include larger changes, such as deletions of a domain or an exon.

Techniques for in vitro mutagenesis of cloned genes are known. Examples of protocols for site specific mutagenesis may be found in Gustin et al., Biotechniques 14:22 (1993); Barany, Gene 37:111-23 (1985); Colicelli et al., Mol Gen Genet 199:537-539 (1985); and Prentki et al., Gene 29:303-313 (1984). Methods for site specific mutagenesis can be found in Sambrook et al., Molecular Cloning: A Laboratory Manual, CSH Press 1989, pp. 15.3-15.108; Weiner et al., Gene 126:35-41 (1993); Sayers et al., Biotechniques 13:592-596 (1992); Jones and Winistorfer, Biotechniques 12:528-530 (1992); Barton et al., Nucl. Acids Res. 18:7349-7355 (1990); Marotti and Tomich, Gene Anal Tech 6:67-70 (1989); and Zhu, Anal. Biochem. 177:120-124 (1989). This may allow a mitochondrial regulatory protein to be expressed in an inactive form. Additionally, the gene expressing a mitochondrial regulator can be ablated using the "knock out" technology as described in U.S. Pat. Nos. 5,464,764 and 5,487,992, all of which are incorporated herein by reference in their entirety, and specifically incorporated to disclose and describe methods of ablating endogenous genes.

Any of the well-known methods for suppressing expression of protein from a gene may be used including sense suppression, anti-sense suppression and RNAi suppression. For a description of RNAi gene suppression by transcription of a dsRNA see U.S. Pat. No. 6,506,559, U.S. Patent Application Publication No. 2002/0168707 A1, WO 98/53083, WO 99/53050 and WO 99/61631, all of which are incorporated herein by reference. Suppression of an gene by RNAi can be achieved using a recombinant DNA construct having a promoter operably linked to a DNA element comprising a sense and anti-sense element of a segment of genomic DNA of the gene, e.g., a segment of at least about 23 nucleotides, more preferably about 50 to 200 nucleotides where the sense and anti-sense DNA components can be directly linked or joined by an intron or artificial DNA segment that can form a loop when the transcribed RNA hybridizes to form a hairpin structure.

Methods for cultivation of suitable microorganisms and methods for collection of evolved hydrogen are known to the person skilled in the art and are described, for example, in US Patent Application No. 2001/005343, by Melis (Melis, 2000) and in WO03/067213, the contents of which are incorporated herein by reference.

The production of hydrogen is carried out under illuminated conditions. Preferably the light is continuous, with sunlight as the source during daylight hours, and artificial illumination used at night, and in cloudy conditions. Sunlight may also be used alone, with no extra illumination provided at night, although this may decrease the yield of hydrogen.

The production of hydrogen is carried out under "microoxic conditions" which refers conditions in which a minimal oxygen concentration is maintained so as to avoid hydrogenase inactivation, and generally refers to a substantially anaerobic environment. The oxygen may be forced out of the system by addition of helium gas, for example. Alternatively, and more preferably, the system may be initially closed from the external environment, without any removal of the oxygen. The lack of photosynthesis from the alga will naturally decrease the amount of oxygen present in the system over time such that the environment is substantially anaerobic, and efficient generation of hydrogen may then be effected.

As used herein "illuminated conditions" refers to the presence of light at sufficient intensity for photosynthesis to take place. The light may be from an artificial source or natural sunlight. In an embodiment the light intensity is between 15 and 3100 µmol m$^{-2}$ sec$^{-1}$ (and all ranges within this range such as 100-3000, 1000-2000 and so on) and illumination continues for up to 120 hours (but may be for a lesser period such as 24, 48, 64 or 96 hours).

The media used in the invention may be any of the standard commercial preparations used for culturing alga that also contain sulfur. Preferably, TAP media is used. The algae may be cultured in a liquid or solid media, with liquid media being preferred.

EXAMPLE 1

Isolation of Mutant Strains

Strains and Culture Conditions

The *Chlamydomonas reinhardtii* strains WT13 and CC 1618 (arg7 cw15, mt$^-$) were obtained from the *Chlamydomonas* Genetics Center Collection (Duke University, USA). All strains used were cultivated mixotrophically in TAP medium (Tris-acetate-phosphate, pH 7.0) by illumination with 40 µmol m$^{-2}$ sec$^{-1}$ white light at 20° C. (Harris 1989) in a twelve hours light-dark cycle to a cell density of 2×10$^6$ cells per ml.

When required (for the arginine auxotroph strain CC1618) the medium was supplemented with 110 µg arginine per ml.

Mutant Construction and Genetic Analysis

Nuclear transformation was performed as described following the methods of (Kindle et al., 1989) and (Purton and Rochaix, 1995).

Plasmids pARG7.8, containing a 7.8 kb genomic DNA fragment of the *Chlamydomonas reinhardtii* argininosuccinate lyase gene (Debuchy et al. 1989) and a 0.4 kb fragment of bacteriophage φX174 DNA (Gumpel and Purton 1994), were used for transformation experiments. Prior to use pARG7.8 was linearised by digestion with BamHI.

Genetic crosses were performed with WT13 and the mutant as described by Harris (1989).

DNA sequences flanking the tag were cloned by ligation mediated suppression PCR (LMS-PCR) (Strauss et al., 2001) and by plasmid rescue (Tam and Lefebvre, 1993).

Isolation of State Transition Mutants

To identify genes involved in state transitions within *C. reinhardtii*, we screened a library of mutants that can grow on TAP medium lacking arginine, generated after the random insertion of plasmid pArg7.8 carrying the Arg7 gene into the nuclear genome of the arginine auxotrophic strain, CC1618 (Debuchy et al., 1989; Gumpel and Purton, 1994). A plate-based fluorescence video-imaging screen, which involves the recording of chlorophyll fluorescence from individual colonies before and after illumination with light that induces state transitions in WT was used to identify potential state transition mutants (stm) (Kruse et al., 1999). Of the 2×10$^4$ colonies screened, four possible stm mutants were identified, with the mutant Stm6 being demonstrated to have increased hydrogen production.

Fluorescence Video Imaging and 77K Fluorescence Spectroscopy

Screening of the mutants for state transitions defects was performed as described earlier (Kruse et al., 1999) by video imaging with a FluorCam 700 MF apparatus (Photon System Instruments) at room temperature and at 77K with a fluorescence/luminescence spectrometer (Perkin Elmer LS50B). Samples were measured following illumination with 40 µmol m$^{-2}$ s$^{-1}$ white light (state 2) or illumination for 20 min with 710 nm (Schott filter, Germany) PSI light (state 1). Alternatively, cells were adjusted to state 2 by incubation in the dark for 30 min under nitrogen atmosphere according to Bulté et al. (1990).

Algal Culture

WT and Stm6 cell cultures were grown in the dark or under illumination (60 µmol/m$^2$·s$^{-1}$ white light) on TAP agar plates or in TAP medium until a cell density of ~2×10$^6$ cells ml$^{-1}$ was reached.

EXAMPLE 2

Hydrogen Evolution Measurements

H$_2$ concentrations were measured in the liquid phase and the gaseous head space above, both for WT and Stm6 cultures (cell density of OD$_{750\ nm}$=0.8). Dissolved H$_2$ concentrations were measured in 1 liter dark-adapted cell cultures in TAP medium replete with, or depleted of, sulfur using a Clark type hydrogen electrode (Unisense PA2000, Denmark) upon white light illumination. H$_2$ concentrations in the presence and absence of 5 µM carbonylcyanide m-chlorophenylhydrazone (CCCP) were measured using dark adapted cultures (1 h) before and after illumination (white light, 300 µmol m$^{-2}$·s$^{-1}$) The H$_2$ concentration in the gaseous head space was measured using a mass spectrometer (Delta Finnigan MAT). Cell cultures were dark-adapted for 30 min in a weak vacuum to deplete the medium and headspace of O$_2$ and H$_2$, prior to illumination with continuous or pulsed (3.3 Hz frequency, 5 µs flashes; light intensity range of 15-3000 µmol·m$^{-2}$·s$^{-1}$) white light.

Figure 3:
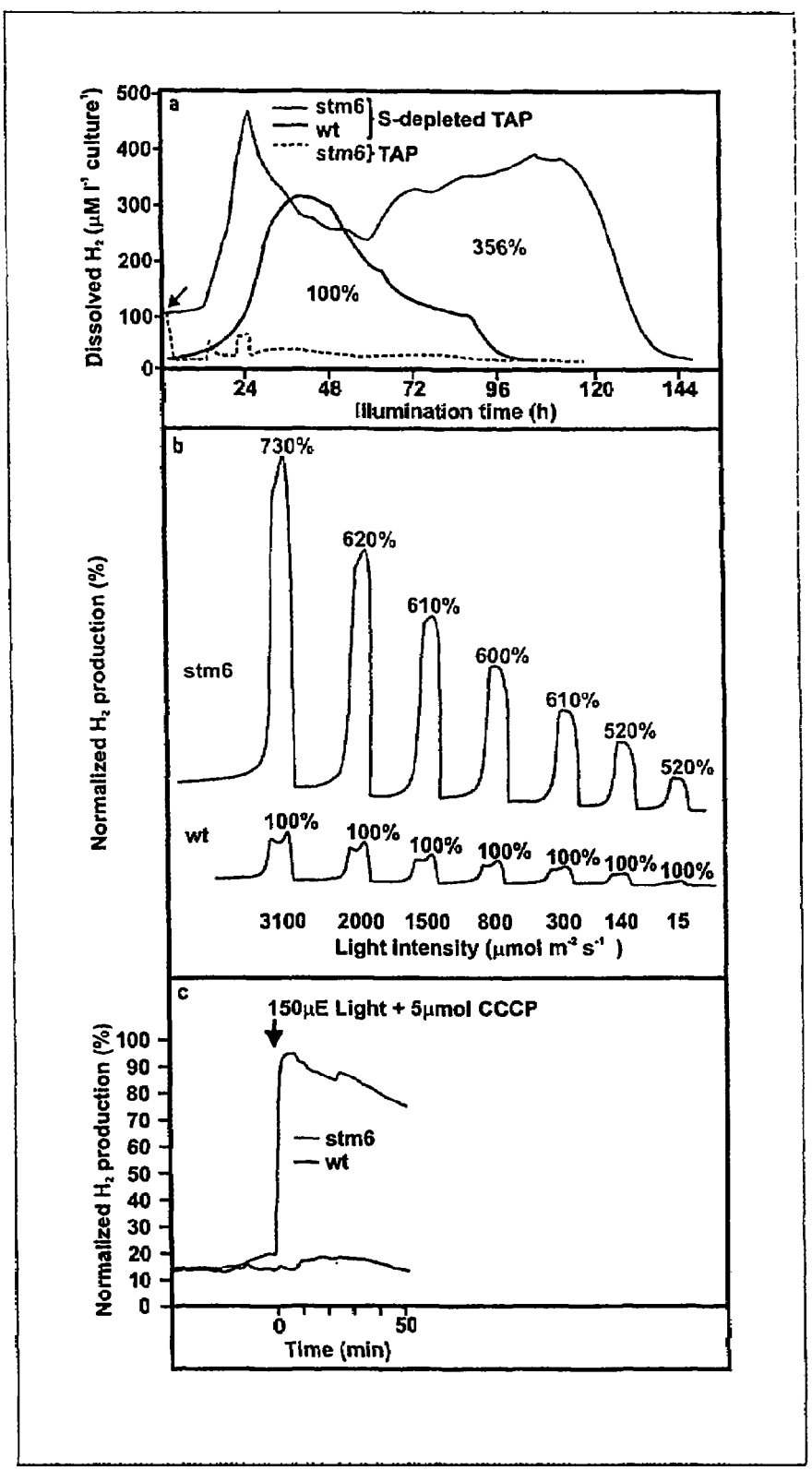
FIG. 3 shows the $H_2$ production properties of wild type (WT) and mutant (M) *C. reinhardtii*: A. Long-term hydrogen production of WT and Stm6 *Chlamydomonas reinhardtii* cultures. Dissolved $H_2$ concentrations were measured using a Clark-type hydrogen sensor system (UniSense, Denmark) and 1 liter dark-adapted cell cultures of WT and Stm6 (equal cell density of $OD_{750\ nm}=0,8$/illumination). In the absence of Sulphur, Stm6 produced 3.5× more $H_2$ than the WT (i.e. integrated area measurements 146/41=3.5).

With reference to FIG. 3 it will be noted that in the absence of sulfur, Stm6 produced 3.5× more H$_2$ than the WT (i.e. integrated area measurements 146/41=3.5).

The effect of light intensity on hydrogen production of wild type and Stm6 *Chlamydomonas reinhardtii* cultures estimated by gas mass spectrometry were also noted, with H$_2$ evolution (relative rates) by WT and Stm6 cells (dark adapted for 30 min) measured during 1 minute periods of continuous illumination at different irradiance levels. Stm6 consistently showed 500-700% higher rates (as indicated by peak labels) of hydrogen production than the wild type.

The uncoupler CCCP stabilizes H$_2$ production rates at levels ~1500% higher than in the WT, as estimated by hydrogen Clark electrode measurements (UniSense). This indicates that HydA activity may be limited by the rate of substrate supply.

EXAMPLE 3

Measurement of the Evolved Gas Volume during Photosynthetic H$_2$ Production Aim: To determine the volume and composition of gas evolved by Stm6 during photosynthetic H$_2$ production.

Method: The experiment was conducted under white light (80 µmol·m$^{-2}$·s$^{-1}$). The culture was incubated in dark under sulphur deprived conditions for 40 hrs. The cells were grown in TAP medium supplemented with acetate as an additional carbon source, to an OD$_{750}$ (optical density at 750 nm) of ~1.0. The culture volume was 300 ml; the data for the gas evolved is normalized to 1 liter culture. Hydrogen was measured using an Agilent Micro gas chromatograph.

| Culture | Mutant (Stm6) | | | |
|---|---|---|---|---|
| | Gas volume in total L [ml] | Gas volume [ml]/hr | $H_2$ proportion [%] | Total running time |
| Stm6-S[1] | 69.75 | 0.99 | 76% | >69 hrs |

EXAMPLE 4

Oxygen Concentrations Measurements in WT and Stm6 Cultures

Aim: To establish whether the high $H_2$ phenotype of Stm6 could be linked with the ability to maintain a reduced $O_2$ concentration in the culture.

Method:

Dissolved oxygen concentration measurements were performed with a Clark type oxygen electrode (Unisense) to obtain the data shown in FIG. 12 (Panels A and B).

Panel A: Cell cultures were grown to a density of 0.1 µg Chl/ml in sulfur replete TAP medium under constant illumination of 300 µmolm$^{-2}$s$^{-1}$ at time=0, when the cells were transferred to sulfur depleted tap medium.

Panel B: Cellular respiration measurements were conducted in the dark using light cultivated cell preparations (30 µg Chl/ml)±5 mM KCN.

Results of measurements of cellular oxygen concentrations in WT and Stm6 are shown in FIG. 12:

Time=0 indicates the time at which the cultures were transferred into sulfur depleted medium. At time=0, PSII was not yet inhibited. Despite this, Stm6 cultures maintained a dissolved oxygen concentration of only 40% of that observed in wild type. Subsequently dissolved oxygen concentrations reduced both in wild type and Stm6 cultures in similar measure, until PSII was completely inhibited due to the inability to repair damaged D1 protein in the absence of sulfur.

Respiration rate: to identify whether the reduced dissolved oxygen concentration for Stm6 shown in panel A was in part due to an increased respiration level in Stm6, in addition to reduced PSII activity, respiration levels were measured in the dark (PSII inactive)±5 mM KCN (inhibitor of complex IV). Stm6 was shown to have a respiration rate 60% higher than the wild type, both in the presence and absence of KCN. These results show not only that Stm6 has an increased level of respiration but that oxygen uptake is not mediated by normal oxidative phosphorylation but probably via the alternative oxidate pathway.

Growth Rates Under Low Light Conditions

FIG. 16 gives a comparison of growth rates of Stm6 and wild type under low light levels. In bioreactor condition light levels are often the limiting factor in biomass production. When Stm6 and the wild type growth rates were compared at lower light levels (10 µm m$^{-2}$ s$^{-1}$ at 24° C., 24 hours light) in TAP medium supplemented with acetate, Stm6 grew faster than the wild type. This suggests that Stm6 may have some advantages for biomass production under bioreactor growth conditions.

EXAMPLE 5

Characterisation of Stm6 Mutant (i) Stm6 is Blocked in State 1 and Impaired in PSII-LHCII Phosphorylation Chlorophyll fluorescence assays conducted by fluorescence emission spectroscopy at 77 K (FIG. 5) and chlorophyll video imaging with actinic 620 nm light at room temperature (FIG. 5) revealed that Stm6 was blocked in state 1. In contrast to the WT, light preferentially absorbed by PSII was unable to drive the cells into state 2, which is monitored by an increase in the fluorescence coming from PSI at 720 nm (FIG. 5). A transition to state 2 was also blocked when the PQ pool was driven reduced in the dark through anaerobiosis (data not shown).

Since state 2 is associated with the phosphorylation of threonine residues in the light harvesting (LHC) antenna proteins of PSII (Allen et al., 1981), anti-phosphothreonine antibodies were used to assess the level of phosphorylation in immunoblots. Stm6 showed a marked reduction in the phosphorylation levels of CP29 (P9) and LHC-P11 proteins upon illumination conditions that promote phosphorylation of these proteins in WT (FIG. 5). Control immunoblots confirmed that Stm6 still contained WT levels of LHC proteins (FIG. 5).

To test that the PQ pool could still be reduced in Stm6, chlorophyll fluorescence measurements were performed to determine the photochemical quenching parameter, $q_p$, which is a measure of the reduction state of the PQ pool (Lunde et al., 2000). Under growth light conditions the PQ pool was in a more reduced state in Stm6 compared with WT (1-$q_p$ of 0.77 in Stm6 and 0.59 in WT) (Table 1). The levels of PSI and PSII activity in Stm6 were also similar to that found in WT (Table 1).

(ii) Stm6 is Sensitive to High Light

Besides effects on state transitions, a striking phenotype of the Stm6 mutant was its sensitivity to light stress. After 4 hours illumination by 1000 µmol m$^{-2}$ s$^{-1}$ high light cells of the mutant showed a marked decline in viability whereas the WT and a complemented strain, B13, were nearly unaffected (FIG. 6). Stm6 showed a dramatic increase in singlet oxygen inside the cell upon illumination as assessed by the accumulation of lipid hydroperoxides (Table 1).

TABLE 1

| | WT | Stm6 | B13 |
|---|---|---|---|
| φ PSI activity (thylakoids) | set to 100 | 130 ± 10 | 95 ± 10 |
| φ PSII activity (thylakoids) | set to 100 | 75 ± 15 | 105 ± 10 |
| Chl a/b ratio (cells) | 1.95 ± 0.1 | 1.85 ± 0.1 | 1.9 ± 0.1 |
| MDA concentration | set to 100 | 230 ± 20 | 110 ± 15 |
| 1-qp (Fm' − Fs)/(Fm' − Fo') | 0.59 ± 0.02 | 0.77 ± 0.02 | 0.60 ± 0.02 |

(iii) Disruption of a Single-mterf-type Gene in Stm6 is Responsible for the Defect in State Transitions and for Light Sensitivity To test whether the arg marker carried by plasmid pArg7.8 was tightly linked to Stm6, genetic crosses were performed between WT13 and Stm6 and the progeny scored for the ability to grow on arginine-free medium and to do state transitions as assessed by video imaging. In all 50 progeny examined, clones able to grow on arginine-free TAP medium exhibited normal state transitions whereas clones showing arginine auxotrophy also showed impaired state transitions (data not shown). These data suggested that Stm6 was an arg-tagged mutant.

A combination of plasmid rescue and ligation-mediated suppression (LMS)-PCR (Strauss et al., 2001) led to the identification of the site of insertion of the arg marker in Stm6. More detailed analyses revealed that two pArg7.8 plasmids had inserted in tandem into Stm6 (FIG. 7).

Subsequent sequence analysis and homology searches revealed that two genes were affected by the random integration of the pArg7.8 plasmid. One gene was previously described as a nuclear transposon (toc1) (Day et al., 1988), the second gene was unknown and its sequence submitted to GenBank database as mod (Genbank AccNo. AF531421). The correct localisation of the affected genomic insertion site in Stm6 DNA was finally confirmed by sequencing and PCR analysis (FIG. 7).

The random insertion by non-homologous recombination caused the deletion of approx. 2 kb of genomic DNA including 610 bps at the 3' region of the mod gene and 880 bps at the 5' end of the toc1 gene (FIG. 7).

PCR analysis in Stm6 and WT with a 5'-specific moc1-primer and a second primer derived from the nuclear insertion sequence resulted in the amplification of a 1005 bp PCR product in Stm6. This confirmed that the insertion caused the deletion of only parts of moc1 leaving the 5' region of the gene untouched. The identification of remaining 512 bps of moc1 on the 5' region of the nuclear insertion and of remaining 4782 bps of toc1 on the 3' region of the nuclear insertion in Stm6 clearly demonstrated that the mutation is entirely restricted to the 3'-moc1/5'-toc1 gene region and did not affect any other possible adjacent coding regions.

Complementation experiments confirmed that the single copy of moc1 was responsible for the lack of state transitions in Stm6 (see FIGS. 5, 6, 9). The complemented strain B13 was isolated in a co-transformation approach using a moc1-containing cosmid in combination with a second vector containing the cry1 gene conferring emetine resistance as a dominant selectable marker (Nelson et al., 1994). The 37 kb cosmid was isolated from a cosmid library (kind gift of Dr. Saul Purton, UCL, UK). Sequence analysis of the insertion region revealed that moc1 was the only gene inserted into the cosmid.

Of approximately 5000 emitine-resistant colonies assessed, four were found to perform normal state transitions (assessed by fluorescence video imaging) and all four contained the moc1 gene.

The moc1 gene encodes a 35 kDa protein containing somewhat surprisingly a putative mitochondrial transit sequence and two mitochondrial transcription termination factor domains (mterf) with leucine zipper motifs characteristic of DNA-binding proteins (Daga et al., 1993). Overall there were striking similarities to the 35 kDa human mTERF protein (34% based on alignments covering the full length sequences) (FIG. 8) and their homologues in *Drosophila melanogaster* (DmTTF, Roberti et al., 2003) and sea urchin (mtDBP, Loguericio et al., 1999). Human mTERF binds downstream of tRNA genes and is thought to be involved in controlling the amount of tRNA and rRNA synthesised within the mitochondrion as well as the expression of other mitochondrial genes and consequently the functionality of the mitochondrial respiratory chain (Fernandez-Silva et al., 1997; Selwood, 2000; Hess et al., 1991). Interestingly 9 homologues to MOC1 with mterf domains have been identified in the genome of *Arabidopsis thaliana*, four of which are predicted to be targeted to the mitochondrion (At1g61980, At2g44020, At4g02990, At2g03050) and one to the chloroplast (At5g55580). Analysis of the recently released *Chlamydomonas* nuclear genome data-base, plus DNA hybridisation experiments, suggest that there is only one copy of moc1 in *C. reinhardtii*.

(iv) MOC1 is a Mitochondrial Protein and its Absence Affects the Expression of Cytochrome Oxidase Anti-peptide antibodies raised against MOC1 were used to confirm that MOC1 was indeed targeted to the mitochondrion rather than the chloroplast (FIG. 9) and that it was absent in the Stm6 mutant. Importantly expression of MOC1 was up-regulated at both the RNA and protein level upon a dark to light transition (FIG. 10).

Experiments were performed to assess whether the absence of MOC1 had affected the expression of mitochondrial respiratory complexes. Immunoblots revealed that accumulation of subunit 90 of cytochrome oxidase (Lown et al., 2001) (COX90) was reduced in Stm6 (FIG. 9) whereas levels of soluble Cytochrome C were unaffected and levels of the Alternative oxidase 1 (AOX1) even increased by the mutation (FIG. 9). In the complemented strain, B13, subunit 90 of cytochrome oxidase were restored to almost WT levels. The immunoblot data agreed well with activity measurements for cytochrome oxidase in mitochondria isolated from dark-grown WT and Stm6 cells (FIG. 10). Following the light treatment, there was a dramatic decrease in cytochrome oxidase activity in Stm6. Levels of ATP in light-grown Stm6 cells were at about 50% of the levels of the WT and B13 (FIG. 10), consistent with a role for cytochrome oxidase in the generation of ATP from photosynthetically derived reductant, in line with earlier suggestions (Krömer and Heldt, 1991).

(v) MOC1 is Involved in Changing the Transcription of the Mitochondrial Genome Upon Exposure to Light Given that MOC1 encodes a transcription factor homologous to human mTERF, experiments were directed at detecting possible perturbations to the transcript profile of the mitochondrial genome, which for *C. reinhardtii* consists of a 15.8 kb linear genome (Gray and Boer, 1988). A number of respiratory subunits are encoded by the genome including subunit 1 of cytochrome oxidase (cox1 gene product), 5 subunits of complex I (nad1-2, nad4-6 gene products), and apocytochrome b (cob gene product).

Semi-quantitative RT-PCR analysis of the nad2 and cox1 genes revealed dramatic differences in transcript levels between WT and Stm6 following exposure of dark-grown cells to light. Compared to the WT, Stm6 consistently showed reduced levels of the cox1 transcript and higher levels of the transcript derived from the nad2 gene, located immediately downstream of cox1 (FIG. 10).

Together these results suggest an important role for MOC1 in controlling the level of cytochrome oxidase activity at the level of transcription of cox1. Since COX1 is the first subunit to be assembled into the cytochrome oxidase complex, the level of COX1 expression is likely to be an important determinant of the amount of enzyme synthesised (Nijtmans et al., 1998).

(vi) A Model for the Role of MOC1 in the Regulation of the Mitochondrial Respiratory Chain during Light Stress A model for the role of MOC1 in mitochondrial function is presented in FIG. 11. The mitochondrial genome is transcribed bi-directionally to give two primary transcripts, which are then processed into smaller transcripts (Gray and Boer, 1988). Our results show that MOC1 is important for maintaining a high level of cox1 mRNA with respect to the downstream nad2 transcript. A possible binding site for MOC1, which is likely to be a transcription termination factor, would therefore be between cox1 and nad2. The diversity of binding sites for this class of transcription factors make it difficult at this stage to predict a possible binding site for MOC1 (Roberti et al., 2003).

In our model the activity of MOC1 would allow the mitochondrion to disconnect the transcription of cox1 from the downstream nad genes so as to increase the relative expression of COX1 needed for the synthesis of additional cytochrome oxidase complexes. This is particularly relevant given that rotenone-insensitive mitochondrial NADH dehydrogenases, unrelated to Complex I, might be induced in the light (Svensson and Rasmussen, 2001) so that there would be a need for the synthesis of more cytochrome oxidase. Given that there might be more than one binding site for MOC1 per genome (Roberti et al., 2003) and there is potential for binding to RNA as well as DNA, the effects of MOC1 activity on mitochondrial gene expression might be rather complex.

(vii) Cyclic Electron Transport Measurements

AIM: To determine whether cyclic electron transport is inhibited in Stm6 under aerobic and anaerobic conditions.

Method:

Cyclic electron transport rates (FIG. 14) were determined spectroscopically by measuring the light induced redox changes of cyt f in the presence of either 20 μM dichlorophenyl dimethyl urea (DCMU: inhibits $e^-$ transport from PSII to $cytb_6f$) or 5 μM 2,5-dibromo-6-isopropyl-3-methyl-1,4-benzoquinone (DBMIB: inhibits $e^-$ transport from $cytb_6f$ to Plastocyanin) PSI and PSII activities were estimated spectroscopically from charge separation measurements after a single turnover flash excitation. For this purpose cells were dark adapted for 2 h, or illuminated for 10 min with 200 $\mu mol/m^2 \cdot s^{-1}$ white light, before measurements. (Trebst et al (1980))

Thus, Cyclic electron transport measurements involving $Cyt_f$ redox state changes show that cyclic $e^-$ transport is inhibited in Stm6 both under aerobic and anaerobic conditions (viii) PSII Activity Levels AIM: To determine whether PSII activity levels are down regulated in the light due to the large antenna size of PSII in state 1

Method: PSI and PSII activities (FIG. 14) were estimated spectroscopically from charge separation measurements after a single turnover flash excitation. For this purpose cells were dark adapted for 2 h, or illuminated for 10 min with 200 $\mu mol/m^2 \cdot s^{-1}$ white light, before measurements.

In dark adapted cultures, WT and Stm6 cells had similar PSII (PSII-D) and PSI (PSI-D) activity. As expected PSI activity levels remained constant (PSI-L) on pre-illumination for 10 minutes. In contrast the 10 min pre-illumination step resulted in photoinhibition of PSII (PSII-L) both in the WT and Stm6. This indicates that PSII is sensitive to photoinhibition. However in the case of Stm6 the inactivation was more marked (PSII-L) due to the large PSII antenna size of Stm6, being in the state 1 transition (Finnazzi et al (2003)).

(ix) Malate Dehydrogenase Down Regulation

Efforts were made to establish whether the activity of malate NADPH dehydrogenase which is involved in the transfer of $H^+$ and $e^-$ from the chloroplast to the mitochondria was down regulated in Stm6. Down regulation would be an indication that $H^+$ and $e^-$ remain in the chloroplast for $H_2$ production via HydA rather than being fed into the mitochondria. As seen in FIG. 15, Malate NADPH-dehydrogenase activity measurements in WT and Stm6 cell cultures showed that the activity of this enzyme was down regulated in Stm6 (Lemaire et al (2003)).

Discussion

To achieve $H_2$ production, three conditions must be fulfilled. First the oxygen induced inhibition of HydA must be lifted. Second, the stromally located HydA must have a high rate of substrate ($H^+$ and $e^-$) supply. Third, as the delivery of $e^-$ to the stroma involves PSI, optimal $H_2$ production via HydA, requires light. In summary, biohydrogen production via HydA occurs under a state of "anaerobic photosynthesis" (FIG. 2).

Figure 1:
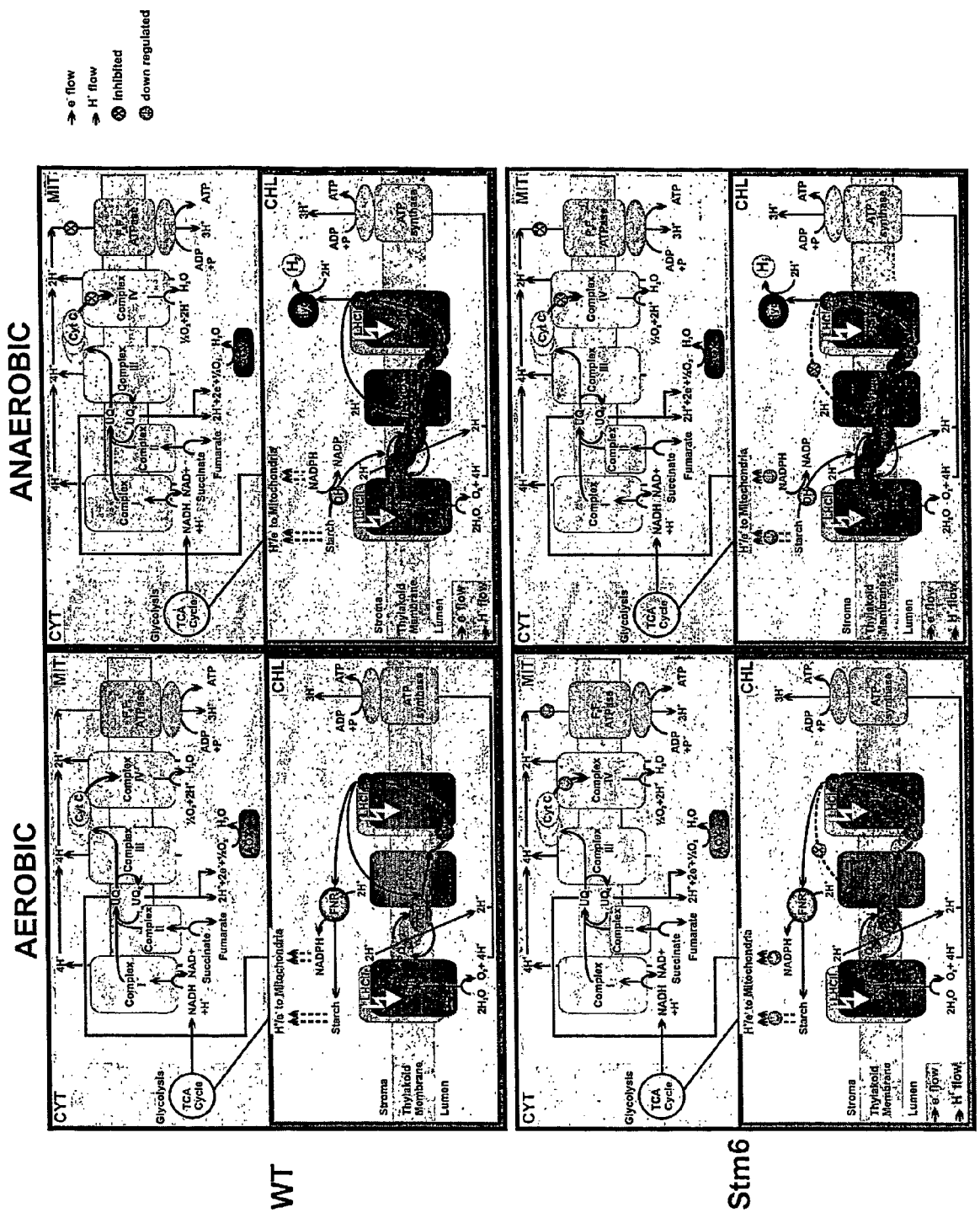
FIG. 1 is a diagrammatic representation of the biochemical pathways related to photosynthetic $H_2$ production in Stm6 and WT under aerobic and anaerobic conditions. The labelled compartments represent the chloroplast (CHL), cytosol and mitochondria (MIT), respectively. Dark and light arrows represent electron and proton flow, respectively, and alternatively dark and light lines indicate simultaneous proton and electron flow. Black crosses on a circle indicate inhibited pathways. Black arrows on a circle indicate down regulated pathways.
Figure 2:
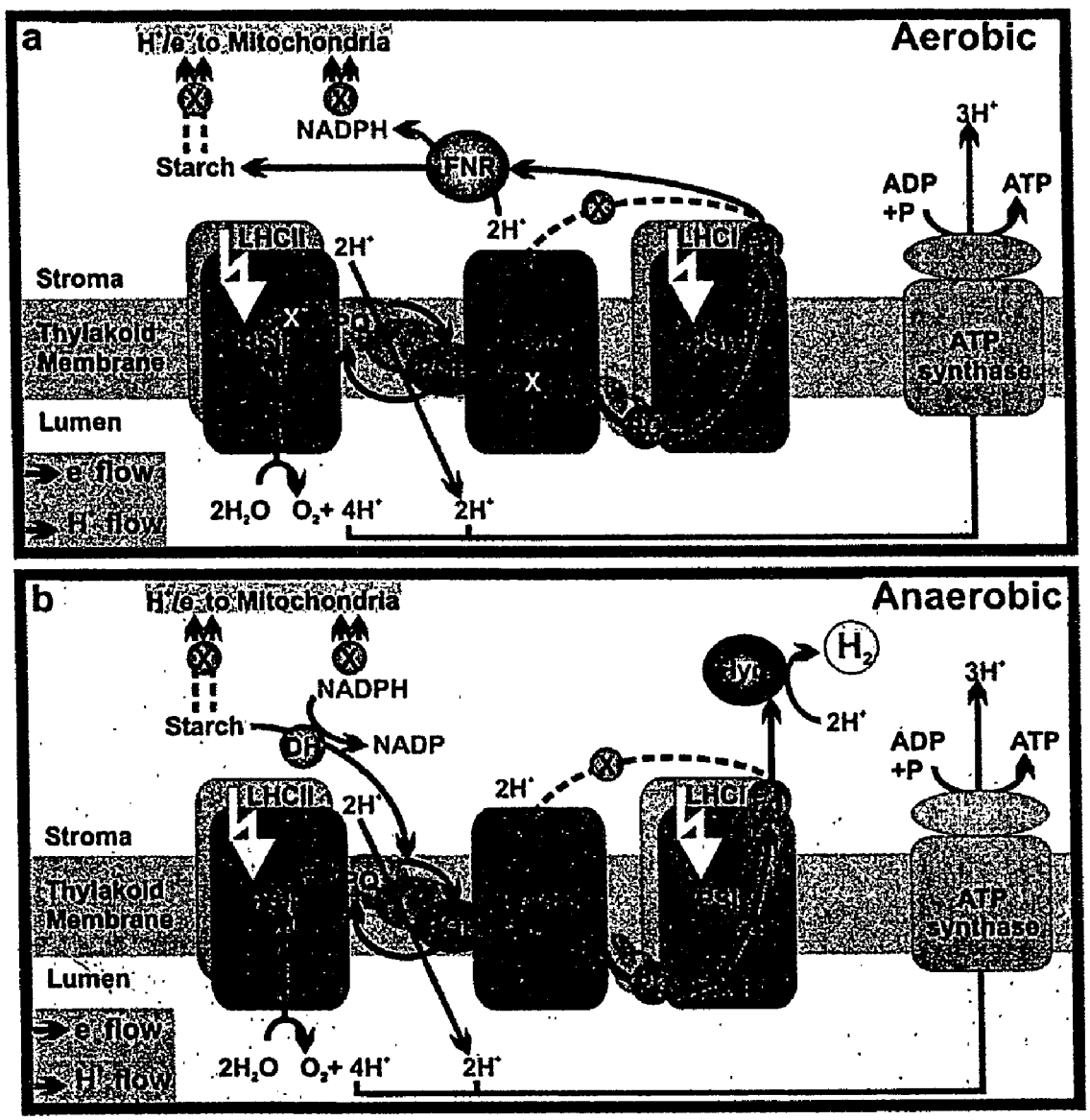
FIG. 2 shows $H^+/e^-$ flow in the chloroplast of *C. reinhardtii* under aerobic and anaerobic conditions. a, under aerobic conditions electrons derived from the water splitting reaction of PSII are passed along the photosynthetic electron transport chain (solid black arrows) via plastoquinone (PQ), cytochrome $b_6f$ (Cyt $b_6f$), Photosystem I (PSI) and ferrodoxin (Fd) before being used in the production of NADPH and starch. $H^+$ released into the thylakoid lumen by PSII and the $PQ/PQH_2$ cycle (proton flow indicated by solid light grey arrows), generate a proton gradient which drives ATP production via ATP synthase. Dashed lines indicate $H^+$ (light grey) and $e^-$ (black) transfer pathways inhibited in Stm6. b, under anaerobic conditions, $H^+/e^-$ stored in starch and NADPH are fed to HydA for $H_2$ production. In Stm6, cyclic electron transport (dashed black line connecting Fd and Cyt $b_6f$), is inhibited.

To enable the rapid identification of mutants with an improved $H_2$ production capacity, C. reinhardtii knock outs were first screened for a disrupted state transition process (FIG. 2). This process normally balances PSI and PSII turnover rates (FIG. 1), by regulating the size of their light harvesting antennae (LHCI & LHCII, respective), specifically by shuttling Lhcb proteins between the two photosystems (State 1: large PSII antenna; State 2: large PSI antenna). In C. reinhardtii, this process results in a switch from linear to cyclic photosynthetic electron transport, which could compete with HydA for $e^-$ at the reducing side of PSI (FIG. 2). Cells blocked in state 1 under anaerobic conditions do not perform cyclic electron transfer. Under these conditions HydA no longer has to compete with $Cytb_6f$ mediated cyclic electron transport for the electrons derived from PSI (FIG. 2), and an increased efficiency of light-driven $H_2$ production can be expected. Among the selected mutants, Stm6, a nuclear knock out mutant of moc1 (Genbank Accession No. AF531421), was found to be blocked in state 1, to have an increased $H_2$ production capacity (FIG. 3), to be inhibited in cyclic electron transport (FIG. 14), to deposit large quantities of starch ($H^+/e^-$ store for HydA) in the chloroplast (FIG. 4) and to have a reduced PSII activity, attributed to an increased sensitivity to photoinhibition due to the constantly large PSII-LHCII antenna complex. In addition, Stm6 exhibited a ~60% reduction in cellular oxygen concentration, likely to be due to the increased activity of alternative oxidase. This diverse and complex set of phenotypic properties essentially primes Stm6 for the conversion of captured solar energy to chemical energy, in the form of $H_2$, via an "anaerobic photosynthetic pathway" driven mainly by PSI.

Moc1 is a nuclear encoded mitochondrial DNA binding protein and its deletion results in the de-regulation of the mitochondrial electron transport pathway in the light. In particular, Moc1 deletion causes a drastic down-regulation of Complex IV. This mutation also results in a drop in mitochondrial electron transport (Complex I→Complex IV), in the ability to maintain the mitochondrial $H^+$ gradient and to synthesise ATP via the mitochondrial $F_0F_1$ ATPase. It therefore drastically reduces the capacity of the mitochondrion to act as a sink for the products of photosynthesis (FIG. 2). Due to this reduced interaction between the mitochondrion and the chloroplast, Stm6 feeds the $H^+/e^-$ derived from PSII to the hydrogenase HydA using the $H_2$ produced as a volatile $H^+/e^-$ sink. The observed semi-autonomous function of the chloroplast in Stm6, and the concomitant inhibition of photosynthetic cyclic electron flow provide an ensemble of valuable attributes that explain the increased $H_2$ production observed in this strain.

Long term (6 days) $H_2$ production experiments (FIG. 3) identified a number of benefits of Stm6 for biohydrogen production. First, in the absence of sulfur (to inhibit PSII repair) hydrogen production was initiated earlier than in the wild type (WT). Second, Stm6 achieved higher $H_2$ production rates. Third, hydrogen production was extended from ~45 hrs (WT) to ~120 hrs (Stm6). Together these three observed improvements resulted in an ~350% increase in $H_2$ production over the WT. It has also been noted that prior to illumination the cultures had been dark adapted for 2 hrs. $H_2$ production was observed in Stm6 shortly after the start of the illumination phase. The importance of this finding is that it suggests that the respiration rate of Stm6 is sufficiently high to prevent the oxygen induced inhibition of HydA expression.

Stm6 has the potential for further yield improvements, with shorter experiments showing a ~500-700% increase in hydrogen production over the WT, throughout an illumination range of 15-3100 $\mu mol/m^2 \cdot s^{-1}$. This is important as it shows that Stm6 also has benefits in terms of its use in a hydrogen bioreactor, in which cells can be exposed to a wide range of illumination intensities, depending upon their distance from the light source.

In contrast to the WT, still higher yields of $H_2$ can be achieved using Stm6, by increasing the rate of substrate ($H^+/e^-$) supply to HydA. Due to the alkalinisation of the stroma during photosynthesis, $H^+$ supply to the stromally located HydA could limit the rate of $H_2$ production (FIG. 2) particularly in Stm6, where the rate of electron delivery to HydA is higher than in the WT, owing to the inhibition of cyclic flow. To test this hypothesis CCCP, a protonophore thought to aid the rapid transport of $H^+$ across the thylakoid membrane, was added to Stm6 and WT cultures. Whereas CCCP had hardly any effect on the WT (presumably because $e^-$ transport was limiting $H_2$ production), Stm6 exhibited an ~1500% increase in $H_2$ production for a period of at least 30 min. This result clearly indicates that $H^+$ transport from the lumen to the stroma is a rate limiting step to improved $H_2$ production in Stm6.

In summary, Stm6 has a number of valuable attributes, for the development of future solar powered $H_2$ production systems capable of using $H_2O$ as a substrate. First, the chloroplasts of Stm6 function semi autonomously, feeding the $H^+$ and $e^-$ derived from $H_2O$ to HydA for $H_2$ production, rather than into the mitochondrial electron transport chain. Second, as cyclic electron transport is switched off in Stm6 this mutant provides a permanent and fast route for the supply of $e^-$ to HydA. Third, Stm6 maintains low cellular $O_2$ concentrations, resulting in a marked increase in HydA activity. Finally, we have shown that Stm6 is capable of producing $H_2$ at a rate 15x higher than the WT in the presence of CCCP. This 15 fold increase is a major step forward in the development of economically viable $H_2$ production systems.

It will be apparent to the person skilled in the art that while the invention has been described in some detail for the purposes of clarity and understanding, various modifications and alterations to the embodiments and methods described herein may be made without departing from the scope of the inventive concept disclosed in this specification.

REFERENCES

The disclosure of the following documents is incorporated herein through reference:

Abraham, S. National Hydrogen Energy Roadmap. *United States Department of Energy* (2002).

Allen, J. F., Bennett, J., Steinback, K. E. and Arntzen, C. J. (1981) Chloroplast protein phosphorylation couples plastoquinone redox state to distribution of excitation energy between photosystems. *Nature* 291, 21-25.

Armstead, H. C. H. *Geothermal Energy: Its Past, Present, and Future Contribution to the Energy Needs of Man* (E. & F. N. Spon, London, 1983).

Bonaventura, C. and Myers, J. (1969) Fluorescence and oxygen evolution from *Chlorella pyrenoidosa*. *Biochim. Biophys. Acta* 189, 366-386.

Bulté, L., Gans, P., Rebéille, F. and Wollman, F.-A. (1990) ATP control on state transitions in vivo in *Chlamydomonas reinhardtii*. *Biochim. Biophys. Acta* 1020, 72-80.

Daga, A., Micol, V., Hess, D., Aebersold, R. and Attardi, G. (1993) Molecular characterization of the transcription termination factor from human mitochondria. *J. Biol. Chem.* 268(11), 8124-8130.

Day, A., Schirmer-Rahire, M., Kuchka, M. R., Mayfield, S. P. and Rochaix, J. D. (1988) A transposon with an unusual arrangement of long terminal repeats in the green alga *Chlamydomonas rheinhardtii*. *EMBO J.* 7 (7), 1917-1927.

Debuchy, R., Purton, S. and Rochaix, J.-D. (1989) The argininosuccinate lyase gene of *Chlamydomonas reinhardtii*: an important tool for nuclear transformation and for correlating the genetic and molecular maps of the ARG7 locus. *EMBO J.* 8, 2803-2809.

De Vitry, C., Finazzi, G., Baymann, F. and Kallas, T. (1999) Analysis of the nucleus-encoded and chloroplast-targeted rieske protein by classic and site-directed mutagenesis of *Chlamydomonas*. *Plant Cell* 11(10), 2031-2044

Depège, N., Bellafiore, S. and Rochaix, J.-D. (2003) Role of chloroplast protein kinase Stt7 in LHCII phosphorylation and state transition in *Chlamydomonas*. *Science* 299, 1572-1575.

Duby, F. and Matagne, R. F. (1999) Alteration of dark respiration and reduction of phototrophic growth in a mitochondrial DNA deletion mutant of *Chlamydomonas* lacking cob, nd4, and the 3' end of nd5. *Plant Cell* 11, 115-125.

Dutilleul, C., Driscoll, S., Cornic, G., DePaepe, R., Foyer, C. H. and Noctor, G. (2003) Functional mitochondrial complex I is required by tobacco leaves for optimal photosynthetic performance in photorespiratory conditions and during transients. *Plant Physiol.* 131, 264-275.

Fernandez-Silva, P., Martinez-Azorin, F., Micol, V. and Attardi, G. (1997) The human mitochondrial transcription termination factor (mTERF) is a multizipper protein but binds to DNA as a monomer, with evidence pointing to intramolecular leucine zipper interactions. *EMBO J.* 16(5), 1066-1079.

Finazzi, G., Rappaport, F., Furia, A., Fleischmann, M., Rochaix, J.-D., Zito, F. and Forti, G. (2002) Involvement of state transitions in the switch between linear and cyclic electron flow in *Chlamydomonas reinhardtii*. *EMBO Rep.* 3(3), 280-285.

Finazzi, G., Chasen, C., Wollman, F. A. & de Vitry, C. Thylakoid targeting of Tat passenger proteins shows no delta pH dependence in vivo. EMBO J. 22:807-15 (2003).

Fleischmann, M. M., Ravanel, S., Delosme, R., Olive, J., Zito, F., Wollman, F. A. and Rochaix, J.-D. (1999) Isolation and characterization of photoautotrophic mutants of *Chlamydomonas reinhardtii* deficient in state transition. *J. Biol. Chem.* 274(43), 30987-30994

Florin, L., Tsokoglou, A., and Happe, T. (2001) *J Biol Chem* 276, 6125-6132

Flügge, U.-I. (1998) Metabolite transporters in plastids. *Curr. Opin. Plant Biol.* 1, 201-206.

Gans, P. and Wollman, F.-A. (1995) The effect of cyanide on state transitions in *Chlamydomonas reinhardtii*. *Biochim. Biophys. Acta* 1228, 51-57.

Ghirardi, M. L., Togasaki, R. K., and Seibert, M. (1997) *Applied Biochemistry and Biotechnology* 63-5, 141-151

Gray, M. W. and Boer, P. H. (1988) Organization and expression of algal (*Chlamydomonas reinhardtii*) mitochondrial DNA. *Phil. Trans. R. Soc. Lond. B* 319, 135-147.

Gu, D. M. and Newton, K. J. (1993) Analysis of Leaf Sectors in the NCS6 Mitochondrial Mutant of Maize. *Plant Cell* 5, 963-971.

Gumpel, N. J. and Purton, S. (1994) Playing tag with *Chlamydomonas*. *Trends Cell Biol* 4, 299-301.

Happe, T., and Kaminski., A. (2002) *Eur J Biochem* 269, 1022-1032

Harris, E. (1989) The *Chlamydomonas* Sourcebook: A Comprehensive Guide to Biology and Laboratory Use. Academic Press, San Diego, USA.

Heldt, W. H., Werdan, K., Milovancev, M. & Geller, G. Alkalization of the chloroplast stroma caused by light-dependent proton flux into the thylakoid space. *Biochim Biophys Acta* 314, 224-41 (1973).

Hess, J. F., Parasi, M. A., Bennett, J. L. and Clayton, D. A. (1991) Impairment of mitochondrial transcription termination by a point mutation associated with the MELAS subgroup of mitochondrial encephalomyopathies. *Nature* 351, 236-239.

Hoefnagel, M. H. N., Atkin, O. K. and Wiskich, J. T. (1998) Interdependence between chloroplasts and mitochondria in the light and the dark. *Biochim Biophys. Acta* 1366, 235-255.

Hoffert, M. I. et al. Energy implications of future stabilization of atmospheric $CO_2$ content. *Nature* 395, 881-884 (1998).

Horton, P., Allen, J. F., Black, M. T. and Bennett, J. (1981) Regulation of phosphorylation of chloroplast membrane polypeptides by the redox state of plastoquinone. *FEBS Lett.* 125, 193-196.

Husic, D. W. and Tolbert, N. E. (1987) Inhibition of glycolate and D-lactate metabolism in a *Chlamydomonas reinhardtii* mutant deficient in mitochondrial respiration. *Proc. Natl. Acad. Sci. USA* 84, 1555-1559.

Kindle, K. L., Schnell, R. A. Fernandez, E. and Levebvre, P. A. (1989) Stable nuclear transformation of *Chlamydomonas* using the *Chlamydomonas* gene for nitrate reductase. *J. Cell Biol.* 109, 2589-2601.

Krömer, S. and Heldt, H. W. (1991) On the role of mitochondrial oxidative phosphorylation in photosynthesis metabolism as studied by the effect of oligomycin on photosynthesis in protoplasts and leaves of barley. *Plant Physiol.* 95, 1270-1276.

Krömer, S., Stitt, M. and Heldt, H. W. (1988) Mitochondrial oxidative phosphorylation participating in photosynthetic metabolism of a leaf cell. *FEBS Lett.* 226, 352-356.

Kruse, B., Narasimhan, N. and Atardi, G. (1989) Termination of transcription inhuman mitochondria: identification and purification of a DNA binding protein factor that promotes termination. *Cell* 58, 391-397

Kruse, O. Light-induced short-term adaptation mechanisms under redox control in the PS II-LHCII supercomplex: LHC II state transitions and PS II repair cycle. *Naturwissenschaften* 88, 284-92 (2001).

Kruse, O., Nixon, P. J., Schmid, G. H. and Mullineaux, C. W. (1999) Isolation of state transition mutants of *Chlamydomonas reinhardtii* by fluorescence video imaging. *Photosynth. Res.* 61, 43-51.

Lee, J. W., Greenbaum, E. A new oxygen sensitivity and its potential application in photosynthetic $H_2$ production. *Applied Biochemistry and Biotechnology* Vol. 105-108 (2003) 303-313

Lemaire, S. D., Collin, V., Keryer, E., Quesada, A. & Miginiac-Maslow, M. Characterization of thioredoxin, a new type of thioredoxin identified in the genome of *Chlamydomonas reinhardtii*. FEBS Lett 543, 87-92 (2003).

Loguericio, P. P., Roberti, M., Musicco, C., Gadaleta, M. N., Quagliariello, E. and Cantatore, P. (1999) Cloning and characterisation of mtDBP, a DNA-binding protein which binds two distinct regions of sea urchin mitochondrial DNA. *Nucleic Acids Res.* 27, 1890-1899.

Lown, F. J., Watson, A. T. and Purton, S. (2001) *Chlamydomonas* nuclear mutants that fail to assemble respiratory or photosynthetic electron transfer complexes. *Biochem. Soc. Trans.* 29(4), 452-455.

Melis, A., Zhang, L. P., Forestier, M., Ghirardi, M. L., and Seibert, M. (2000) *Plant Physiology* 122, 127-135

Melis, A., and Happe, T. (2001) *Plant Physiol* 127, 740-748

Michel, K.-P., Krüger, F., Pühler, A. and Pistorius, E. K. (1999) Molecular characterisation of idiA and adjacent genes in the cyanobacteria *Synechococcus* sp. strains PCC6301 and PCC 7942. *Microbiology* 145, 1473-1484.

Millenaar, F. F. and Lambers, H. (2003) The alternative oxidase: In vivo regulation and function. *Plant Biol.* 5, 2-15.

Miyamoto, K. in *FAO Agricultural Services Bulletin* (ed. Miyamoto, K.) (FAO—Food and Agriculture Organization of the United Nations, Osaka University, Osaka, Japan, 1997).

Murata, N. (1969) Control of excitation transfer in photosynthesis. I. Light-induced change of chlorophyll a fluorescence in *Porphyridium cruentum*. *Biochim. Biophys. Acta* 172, 242-251.

Nelson, J. A. E., Savereide, P. B. and Lefebvre, P. A. (1994) The CRY1 Gene in *Chlamydomonas reinhardtii*: Structure and use as a dominant selectable marker for nuclear transformation. *Mol. Cell. Biol.* 14(6), 4011-4019.

Nijtmans, L. G. J., Taanman, J.-W., Muijsers, A. O., Speijer, D. and Van Den Bogert, C. (1998) Assembly of cytochrome-c oxidase in cultured human cells. *Eur. J. Biochem.* 254, 389-394.

Nurani, G., Erikson, M., Knorpp, C., Glaser, E. and Franzen, L.-G. (1997) Homologous and heterologous import into mitochondria isolated from the green alga *Chlamydomonas reinhardtii*. *Plant Mol. Biol.* 35, 973-980.

Petit, J. R. et al. Climate and atmospheric history of the past 420,000 years from the Vostok ice core, Antarctica. *Nature* 399, 429-436 (1999).

Pfannschmidt, T., Nilsson, A. and Allen, J. (1999) Photosynthetic control of chloroplast gene expression. *Nature* 397(6720), 625-628.

Purton, S. and Rochaix, J. D. (1995) Characterisation of the Arg7 gene of *Chlamydomonas reinhardtii* and its application to nuclear transformation. *Eur. J. Phycol.* 30, 141-148.

Rasmusson, A. G. and Møller, I. M. (1991) NAD(P)H dehydrogenases on the inner surface of the inner mitochondrial membrane studied using inside-out submitochondrial particles. *Physiol. Plant.* 83, 357-365.

Rebeille, F. and Gans, P. (1988) Interaction between chloroplasts and mitochondria in microalgae. *Plant Physiol.* 88, 973-975.

Rifkin, J. *The Hydrogen Economy* (Penguin Putnam Inc., New York, 2002).

Rintamäki, E., Martinsuo, P., Pursiheimo, S. and Aro, E. M. (2000) Cooperative regulation of lightharvesting complex II phosphorylation via the plastoquinol and ferredoxin-thioredoxin system in chloroplasts. *Proc. Natl. Acad. Sci. USA* 97(21), 11644-11649.

Roberti, M., Polosa, P. L., Bruni, F., Musicco, C., Gadaleta, M. N. and Cantatore, P. (2003) DmTTF, a novel mitochondrial transcription termination factor that recognises two sequences of *Drosophila melanogaster* mitochondrial DNA. *Nucl. Acids Res.* 31, 1597-1604.

Rupprecht, J., Kruse, O. & Hankamer, B. Evaluating the feasibility of implementing a global zero-$CO_2$ emission energy strategy. *Energy* (submitted) (2004).

Schönfeld, C. et al. MOC1, a transcription factor essential for mitochondrial light acclimation in *C. reinhardtii*. *J Biol Chem* (submitted) (2004).

Selwood, S. P., Chrzanowska-Lightowlers, Z. M. A. and Lightowlers, R. N. (2000) Does the mitochondrial trancription termination complex play an essential role in controlling differential transcription of mitochondrial DNA? *Biochem. Soc. Trans.* 28(2), 154-159.

Singh, D. P. and Varna, K. (1995) Response of the wild-type and high light-tolerant mutant of *Anacystis nidulans* against photooxidative damage: Differential mechanism of high light tolerance. *Photochem. Photobiol.* 62(2), 314-319.

Stephenson, M., and Stickland, L. H. (1931) *Biochem J.* 25, 205-214

Strauss, C., Mussgnug, J. and Kruse, O. (2001) *Ligation-mediated suppression-PCR as a powerful tool to analyse nuclear gene sequences in the green alga Chlamydomonas reinhardtii. Photosynth. Res.* 70, 311-320

Svensson, A. S. and Rasmusson, A. G. (2001) Light-dependent gene expression for proteins in the respiratory chain of potato leaves. *Plant J.* 28, 73-82.

Tam, L. W. and Lefebvre, P. A. (1993) The use of DNA insertional mutagenesis to clone genes in *Chlamydomonas*. *Genetics* 135, 375-384.

Thomas, C. D. et al. Extinction risk from climate change. *Nature* 427, 145-148 (2004).

Trebst, A. (1980) Inhibitors in electron flow: tools for the functional and structural localization of carriers and energy conversion sites. *Methods Enzymol.* 69, 675-715

Vener, A. V., van Kann, P. J., Rich, P. R., Andersson, B. and Ohad, I. (1997) Plastoquinol at the Qo-site of reduced cytochrome $b_6$/f mediates signal transduction between light and thylakoid phosphorylation. Thylakoid protein kinase deactivation by a single turnover flash. *Proc. Natl. Acad. Sci. USA* 94, 1585-1590

Vener, A. V., Rokka, A., Fulgosi, H., Andersson, B. and Herrmann, R. G. (1999) A clophilin-regulated PP2A-like protein phosphatase in thylakoid membranes of plant chloroplasts. *Biochemistry* 38(45), 14955-14965.

Wollman, F. A. State transitions reveal the dynamics and flexibility of the photosynthetic apparatus. *EMBO J* 20, 3623-3630 (2001).

Zerges, W. and Rochaix, J.-D. (1998) Low density membranes are associated with RNA-binding proteins and thylakoids in the chloroplast of *Chlamydomonas reinhardtii*. *J Cell Biol.* 140(1), 101-10.

Zito, F., Finazzi, G., Delosme, R., Nitschke, W., Picot, D. and Wollman, F.-A. (1999) The Qo site of cytochrome b6f complexes controls the activation of the LHCII kinase. *EMBO J.* 18(11), 2961-2969.

The invention claimed is:

1. *Chlamydomonas reinhardtii* Stm6 deposited with the Culture Collection of Algae and Protozoa on 1 Jul. 2003 under Culture Collection of Algae and Protozoa accession number 11/129.

2. A mutant alga of *Chlamydomonas* spp. capable of hydrogen production under illuminated conditions through action of a hydrogenase, where the hydrogenase comprises HydA, and the alga having a mutation of the Moc 1 gene that reduces or eliminates activity of the mitochondrial transcription factor Moc 1, whereby said alga has increased hydrogen production compared to wild-type alga.

3. A mutant alga as claimed in claim 2, wherein the alga is *Chlamydomonas reinhardtii*.

4. A substantially pure culture of a mutant alga of *Chlamydomonas* spp. capable of hydrogen production under illuminated conditions through the action of a hydrogenase, where the hydrogenase comprises HydA, and having a mutation of the Moc 1 gene that reduces or eliminates the activity of the mitochondrial transcription factor Moc 1, whereby said alga has increased hydrogen production compared to wild-type alga.

5. A substantially pure culture as claimed in claim 4, wherein the alga is *Chlamydomonas reinhardtii*.

6. A substantially pure culture of *Chlamydomonas reinhardtii* Stm6 deposited with the Culture Collection of Algae and Protozoa on 1 Jul. 2003 under accession number 11/129.

* * * * *